US012624097B2

(12) United States Patent
Lim

(10) Patent No.: US 12,624,097 B2
(45) Date of Patent: \*May 12, 2026

(54) NUCLEIC ACIDS, VECTORS, AND CELLS THAT ENCODE ANTI-Sp17 ANTIBODIES AND OTHER Sp17 BINDING PROTEINS

(71) Applicant: Medicovestor, Inc., Wilmington, DE (US)

(72) Inventor: Seah Lim, Wilmington, DE (US)

(73) Assignee: MEDICOVESTOR, INC., Wilmington, DE (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/408,386

(22) Filed: Jan. 9, 2024

(65) Prior Publication Data

US 2025/0011403 A1     Jan. 9, 2025

Related U.S. Application Data

(60) Provisional application No. 63/524,806, filed on Jul. 3, 2023.

(51) Int. Cl.
| | |
|---|---|
| *C07K 16/18* | (2006.01) |
| *A61K 39/395* | (2006.01) |
| *A61K 47/68* | (2017.01) |
| *C12N 15/11* | (2006.01) |
| *C12N 15/63* | (2006.01) |
| *C12N 15/86* | (2006.01) |

(52) U.S. Cl.
CPC ............ *C07K 16/18* (2013.01); *A61K 39/395* (2013.01); *A61K 47/6879* (2017.08); *C12N 15/11* (2013.01); *C12N 15/63* (2013.01); *C12N 15/86* (2013.01); *C07K 2317/31* (2013.01); *C07K 2317/55* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,731,168 | A | 3/1998 | Carter et al. |
| 5,877,296 | A | 3/1999 | Hamann et al. |
| 6,565,827 | B1 | 5/2003 | Kaminski et al. |
| 6,897,044 | B1 | 5/2005 | Braslawsky |
| 7,405,077 | B2 | 7/2008 | Lim |
| 7,422,739 | B2 | 9/2008 | Anderson et al. |
| 7,446,190 | B2 | 11/2008 | Sadelain et al. |
| 7,741,465 | B1 | 6/2010 | Eshhar et al. |
| 8,088,387 | B2 | 1/2012 | Steeves et al. |
| 8,277,806 | B2 | 10/2012 | Lindhofer |
| 8,592,562 | B2 | 11/2013 | Kannan et al. |
| 9,062,349 | B2 | 6/2015 | Chiriva-Internati |
| 9,499,629 | B2 | 11/2016 | June et al. |
| 9,505,848 | B2 | 11/2016 | Davis et al. |
| 9,592,562 | B2 | 3/2017 | Harif et al. |
| 9,695,237 | B2 | 7/2017 | Ando et al. |
| 9,862,769 | B2 | 1/2018 | De Goeij et al. |
| 9,970,937 | B2 | 5/2018 | Chiriva-Internati |
| 10,011,858 | B2 | 7/2018 | Igawa et al. |
| 10,322,192 | B2 | 6/2019 | Albone et al. |
| 10,344,050 | B2 | 7/2019 | Gramer et al. |
| 10,517,960 | B2 | 12/2019 | Jakobsen et al. |
| 10,596,270 | B2 | 3/2020 | Stafford et al. |
| 10,597,464 | B2 | 3/2020 | Labrijn et al. |
| 10,729,782 | B2 | 8/2020 | Naito et al. |
| 10,752,683 | B2 | 8/2020 | Ab et al. |
| 10,836,830 | B2 | 11/2020 | Wilson et al. |
| 11,135,305 | B2 | 10/2021 | Carrigan et al. |
| 11,401,348 | B2 | 8/2022 | Lazar et al. |
| 11,597,766 | B2 | 3/2023 | Zugmaier et al. |
| 11,718,671 | B2 | 8/2023 | Zhang et al. |
| 12,116,410 | B1 | 10/2024 | Lim |
| 12,121,587 | B1 | 10/2024 | Lim |
| 12,319,747 | B2 | 6/2025 | Lim |
| 12,364,777 | B2 | 7/2025 | Lim |
| 12,371,494 | B2 | 7/2025 | Lim |
| 2002/0168662 | A1 | 11/2002 | Lim et al. |
| 2004/0071694 | A1 | 4/2004 | Devries et al. |
| 2005/0158828 | A1 | 7/2005 | Braslawsky et al. |
| 2006/0115817 | A1 | 6/2006 | Lim |
| 2006/0148039 | A1 | 7/2006 | Kobayashi et al. |
| 2007/0297978 | A1 | 12/2007 | Chinn |

(Continued)

FOREIGN PATENT DOCUMENTS

| | | |
|---|---|---|
| WO | 2009086320 A1 | 7/2009 |
| WO | 2014/144080 A2 | 9/2014 |

(Continued)

OTHER PUBLICATIONS

Mariuzza, R.A. et al. 'The Structural Basis of Antigen-Antibody Recognition1 Annu. Rev. Biophys. Biphys. Chem. 16:139-159, 1987.*
Rudikoff et al. "Single Amino Acid Substitution Altering Antigen-Binding Specificity" PNAS. 79:1979-1983, 1982.*
Rader et al. PNAS. 95:8910-8915, 1998.*
Goel et al. Plasticity within the Antigen-Combining Site May Manifest as Molecular Mimicry in the Humoral Immune Response. 1 J. Immunol. 173(12)7358-7367, 2004.*
Kahn et al. 'Adjustable Locks and Flexible Keys: Plasticity of Epitope-Paratope Interactions in Germline Antibodies.' J. Immunol. 192:5398-5405, 2014.*

(Continued)

*Primary Examiner* — Nora M Rooney
(74) *Attorney, Agent, or Firm* — HOLLAND & HART LLP

(57) ABSTRACT

This disclosure describes proteins that specifically bind human sperm protein 17 (Sp17) with nanomolar affinity and high specificity. These proteins include a recombinant human anti-Sp17 IgG that is suitable for use as a therapeutic antibody to treat cancers that ectopically express Sp17. Other Sp17-binding proteins are described including antibody fragments, antibody conjugates, and fusion proteins.

20 Claims, 6 Drawing Sheets

Specification includes a Sequence Listing.

(56) References Cited

U.S. PATENT DOCUMENTS

| | | | |
|---|---|---|---|
| 2009/0162380 A1 | 6/2009 | Glaser et al. |
| 2010/0278834 A1 | 11/2010 | Lanzavecchia |
| 2012/0322135 A1 | 12/2012 | Uda et al. |
| 2013/0295113 A1 | 11/2013 | Mytych et al. |
| 2015/0038682 A1 | 2/2015 | Tsurushita |
| 2015/0056680 A1 | 2/2015 | Chang et al. |
| 2015/0274812 A1 | 10/2015 | Swem et al. |
| 2016/0032014 A1 | 2/2016 | Michaels et al. |
| 2017/0073425 A1 | 3/2017 | Grasso et al. |
| 2017/0121420 A1 | 5/2017 | Heidrich et al. |
| 2017/0151281 A1 | 6/2017 | Wagner et al. |
| 2017/0204194 A1 | 7/2017 | Chen et al. |
| 2017/0319690 A1 | 11/2017 | Wang et al. |
| 2018/0346555 A1 | 12/2018 | Orengo et al. |
| 2019/0015508 A1 | 1/2019 | Bobrowicz et al. |
| 2019/0322750 A1 | 10/2019 | Park et al. |
| 2019/0375852 A1 | 12/2019 | Lindhofer et al. |
| 2020/0093909 A1 | 3/2020 | Lanzavecchia et al. |
| 2020/0239550 A1 | 7/2020 | Walker |
| 2020/0283524 A1 | 9/2020 | Xu et al. |
| 2021/0040235 A1 | 2/2021 | Kadouche et al. |
| 2021/0284726 A1 | 9/2021 | Hou et al. |
| 2022/0213196 A1 | 7/2022 | Jooss et al. |
| 2023/0085779 A1 | 3/2023 | Ab et al. |
| 2023/0201210 A1 | 6/2023 | Sliwkowski et al. |
| 2023/0295293 A1 | 9/2023 | Patel et al. |
| 2023/0391882 A1 | 12/2023 | Urech et al. |
| 2025/0011420 A1 | 1/2025 | Lim |
| 2025/0011460 A1 | 1/2025 | Lim |
| 2025/0127942 A1 | 4/2025 | Lim |
| 2025/0205354 A1 | 6/2025 | Lim |
| 2025/0206816 A1 | 6/2025 | Lim |
| 2025/0206817 A1 | 6/2025 | Lim |
| 2025/0206842 A1 | 6/2025 | Lim |
| 2025/0206847 A1 | 6/2025 | Lim |
| 2025/0255994 A1 | 8/2025 | Lim |

FOREIGN PATENT DOCUMENTS

| | | | |
|---|---|---|---|
| WO | 2015/048272 A1 | 4/2015 |
| WO | 2016/111645 A1 | 7/2016 |
| WO | 2017/013231 A1 | 1/2017 |
| WO | 2017/015634 A2 | 1/2017 |
| WO | 2019/016392 A1 | 1/2019 |
| WO | 2022/076669 A1 | 4/2022 |
| WO | 2022/096716 A2 | 5/2022 |
| WO | 2022/116808 A1 | 6/2022 |
| WO | 2022/235622 A2 | 11/2022 |
| WO | 2023/166418 A2 | 9/2023 |
| WO | 2023/212298 A1 | 11/2023 |

OTHER PUBLICATIONS

Poosarla et al. 'Computational De Novo Design of Antibodies Binding to a Peptide With High Affinity.' Biotech. Bioeng. 114(6): 1331-1342, 2017.*
MacCallum et al. "Antibody-antigen interactions: contact analysis and binding site topography", Journal of Molecular Biology, 1996. vol. 262, pp. 732-745.*
De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*
Akbar et al., A compact vocabulary of paratope-epitope interactions enables predictability of antibody-antigen binding, Cell Reports Mar. 16, 2021, 34, 108856.
Almagro & Fransson Humanization of Antibodies, Frontiers in Bioscience, 2008, 13:1619-33.
Altshuler et al., Generation of Recombinant Antibodies and Means for Increasing Their Affinity, Dept. Of. Biochemistry (Moscow), 2010, 75(13):1584-1605.
Caron et al., Engineered Humanized Dimeric Forms of IgG Are More Effective Antibodies, J. Exp. Med., 1992, 176:1191-95.
Casset et al., A peptide mimetic of an anti-CD4 monoclonal antibody by rational design, Biochemical and Biophysical Research Communications, 2003, 307:198-205.
Chiriva-Internati et al., Sperm protein 17 (SP17) in multiple myeloma: opportunity for myeloma-specific donor T cell infusion to enhance graft-versus-myeloma effect without increasing graft-versus-host disease risk, Eur. J. Immunol, Aug. 2001, 31(8):2277-83.
Chiriva-Internati et al., Tumor Vaccine for Ovarian Carcinoma Targeting Sperm Protein 17, Cancer, May 2002, 1;94(9):2447-53.
Edwards et al., The Remarkable Flexibility of the Human Antibody Repertoire; Isolation of Over One Thousand Different Antibodies to a Single Protein, BLyS, J Mol Biol, 2003, 334: 103-118.
Goel et al., Plasticity within the Antigen-Combining Site May Manifest as Molecular Mimicry in the Humoral Immune Response. Journal of Immunology, 2004, 173(12)7358-7367.
Gura, Systems for Identifying New Drugs Are Often Faulty, Science, 1997, 278:1041-1042.
Hasegawa et al., Single Amino Acid substitution in LC-CDR1 induces Russell body phneotype that attenuates cellular protein synthesis through elF2β phosphorylation and thereby downregulates IgG secretion despite operational secretory pathway traffic, MABS, 2017, vol. 9, No. 5, pp. 854-873.
Holm et al., Functional mapping and single chain construction of the anti-cytokeratin 8 monoclonal antibody TS1, Molecular Immunology, 2007, 1075-1084.
Kahn et al., Adjustable Locks and Flexible Keys: Plasticity of Epitope-Paratope Interactions in Germline Antibodies., Journal of Immunology, 2014, 192:5398-5405.
Lim et al., Sperm protein 17 is a novel cancer-testis antigen in multiple myeloma, Blood, Mar. 1, 2001, 97(5):1508-10.
Lippow et al., Computational design of antibody-affinity improvement beyond in vivo maturation, Nature Biotechnology, 2017, 25(10):1171-1176.
Lo et al., Conformational epitope matching and prediction based on protein surface spiral features, BMC Genomics, 2021, vol. 22, Article No. 116.
Marchalonis et al., The antibody repertoire in evolution: Chance, selection, and continuity, Dev & Comp Immunol., 2006, 30:223-247.
Mariuzza. R.A et al., The Structural Basis of Antigen-Antibody Recognition, Ann. Rev. Biophys. Biphys. Chem., 1987, 16:139-159.
Marks et al., How repertoire data are changing antibody science, J. Biol. Chem. 2020, 295(29) 9823-9837.
Poosarla et al., Computational De Novo Design of Antibodies Binding to a Peptide With High Affinity., Biotech. Bioeng. 2017, 114(6}: 1331-1342.
Rader et al., A phage display approach for rapid antibody humanization: Designed combinatorial V gene libraries, PNAS. 1998, 95:8910-8915.
Rudikoff et al., Single Amino Acid Substitution Altering Antigen-Binding Specificity, PNAS, 1982, 79:1979-1983.
Shopes, B., A genetically engineered human IgG mutant with enhanced cytolytic activity, The Journal of Immunology, May 1, 1992, 148(9):2918- 22.
Shopes, B., A genetically engineered human IgG with limited flexibility fully initiates cytolysis via complement, Molecular Immunology, Apr. 1993, 30(6):603-9.
Straughn et al., Expression of Sperm Protein 17 (SP17) in Ovarian Cancer, Int. J. Cancer, Mar. 1, 2004, 108 (6):805-11.
Sulea et al., Application of Assisted Design of Antibody and Protein Therapeutics (ADAPT) improves efficacy of a Clostridium difficile toxin A single-domain antibody, Scientific Reports, 2018, 8(260): 1-11.
Vajda et al., Progress toward improved understanding of antibody maturation, Current Opinion in Structural Biology, 2021, 67 pp. 226-231.
Van Der Neut Kolfschoten, M. et al., Anti-inflammatory activity of human IgG4 antibodies by dynamic Fab arm exchange, Science, Sep. 14, 2007, 317(5844):1554-7.

(56) References Cited

OTHER PUBLICATIONS

Wolff, EA. et al., Monoclonal antibody homodimers: Enhanced antitumor activity in nude mice, Cancer Res., 1993, vol. 53, Issue. 11, pp. 2560-2565.

Zhang et al., Combined real time PCR and immunohistochemical evaluation of sperm protein 17 as a cancer-testis antigen, Eur. J. Haematol, Oct. 2004, 73(4):280-4 (Abstract).

"International Search Report and Written Opinion of the International Searching Authority," issued in connection with Int'l Appl. No. PCT/US2024/036820, dated Oct. 2, 2024 (13 pages).

"International Search Report and Written Opinion of the International Searching Authority," issued in connection with Int'l Appl. No. PCT/US2024/036824, dated Dec. 17, 2024 (20 pages).

"International Search Report and Written Opinion of the International Searching Authority," issued in connection with Int'l Appl. No. PCT/US2024/045707, dated Nov. 1, 2024, (9 pages).

"International Search Report and Written Opinion of the International Searching Authority," issued in connection with Int'l Appl. No. PCT/US2024/052137, dated Feb. 5, 2025 (19 pages).

Altschul, et al., "Gapped BLAST and PSI-BLAST: a new generation of protein database search programs", Nucleic Acids Res., vol. 25, 1997, pp. 3389-3402.

Altschul, et al., "Protein database searches using compositionally adjusted substitution matrices", Febs J., vol. 272, 2005, pp. 5101-5109.

Golay, J., et al., "Role of Fc Core Fucosylation in the Effector Function of IgGI Antibodies", Frontiers in Immunology, vol. 13, Jun. 2022, 929895.

Rossi, et al., "Novel Designs of Multivalent Anti-CD20 Humanized Antibodies as Improved Lymphoma Therapeutics", Cancer res., Oct. 15, 2008, vol. 68, No. 20, pp. 8384-8392.

Shopes, B., "A genetically engineered human IgG with limited flexibility fully initiates cytolysis via complement," Molecular Immunology, vol. 30, No. 6, Apr. 1993, pp. 603-609.

US Patent Office "Office Action", issued in connection with U.S. Appl. No. 18/408,414. dated Jan. 22, 2025 (19 pages).

Yadav, et al., "Fabrication of alkoxysilane substituted polymer-modified disposable biosensing 2 platform: toward sperm protein 17 sensing as a new cancer biomarker", Talanta, Jun. 1, 2022, vol. 243, pp. 507-514.

"International Search Report and Written Opinion of the International Searching Authority," issued in connection with Int'l Appl. No. PCT/US24/61935, dated Mar. 4, 2025 (21 pages).

"Invitation to pay additional fee of the International Searching Authority," issued in connection with Int'l Appl. No. PCT/US2024/036822, dated Sep. 23, 2024, (3 pages).

"International Search Report and Written Opinion of the International Searching Authority," issued in connection with Int'l Appl. No. PCT/US2024/057968, dated May 19, 2025 (15 pages).

"International Search Report and Written Opinion of the International Searching Authority," issued in connection with Int'l Appl. No. PCT/US2025/014057, dated Apr. 15, 2025, (7 pages).

"International Search Report and Written Opinion of the International Searching Authority," issued in connection with Int'l Appl. No. PCT/US2025/014092, dated Apr. 15, 2025 (9 pages).

"International Search Report and Written Opinion of the International Searching Authority," issued in connection with Int'l Appl. No. PCT/US2025/036133, dated Sep. 5, 2025 (12 pages).

Anonymous, https://www.cancer.gov/about-cancer/understanding/what-is-cancer. accessed May 20, 2020. (Year: 2020).

Anonymous. https://en.wikipedia.org/wiki/List_of_cancer_types. accessed May 20, 2020. (Year: 2020).

Bendig, M. M., "Humanization of rodent monoclonal antibodies by CDR grafting.", Methods-Companion to Methods in Enzymology, vol. 8, No. 2, 1995, pp. 83-93.

Chen, C., et al., "Enhancement and destruction of antibody function by somatic mutation: unequal occurrence is controlled by V gene combinatorial associations.", The EMBO journal, vol. 14, No. 12, 1995, pp. 2784-2794.

Cheung, A., et al., "Targeting folate receptor alpha for cancer treatment.", Oncotarget, vol. 7, No. 32, May 27, 2016, pp. 52553-52574.

Colman, P. M., "Effects of amino acid sequence changes on antibody-antigen interactions.", Research in Immunology, vol. 145, No. 1, 1994, pp. 33-36.

Macor, P., et al., Complement activated by chimeric anti-folate receptor antibodies is an efficient effector system to control ovarian carcinoma, vol. 66, No. 7, 2006, pp. 3876-3883.

Paul, WE., "Fundamental Immunology.", 3rd ed. Raven Press, Chap. 9, 1993, pp. 292-295.

Remington: The Science and Practice of Pharmacy, Philadelphia; Lippincott, Williams & Wilkins 2000, 1 pg.

Scaranti, M., et al., "Exploiting the folate receptor a in oncology.", Nature reviews clinical oncology, vol. 17, No. 6, 2020, pp. 349-359.

Vajdos, F. F., et al., "Comprehensive functional maps of the antigen-binding site of an anti-ErbB2 antibody obtained with shotgun scanning mutagenesis.", Journal of molecular biology, vol. 320, No. 2, 2002, pp. 415-428.

Edwards et al., J Mol Biol. 334(1): 103-118 (Year: 2003).

Lloyd et al. Protein Engineering, Design & Selection 22:159-168 (Year: 2009).

Moore et al., mAbs 2(2): 181-189 (Year: 2010).

Piche-Nicholas et al.MABS 10(1): 81-94 (Year: 2018).

Rudikoff et al., Proceedings of the National Academy of Sciences, 79:1979-1983 (Year: 1982).

Wu et al., J. Mol. Biol. 294: 151-162 (Year: 1999).

International Patent Application No. PCT/US2024/045704; International Search Report and Written Opinion mailed Dec. 11, 2024; 17 pages.

International Patent Application No. PCT/US2024/036822; International Search Report and Written Opinion mailed Dec. 17, 2024; 16 pages.

"International Search Report and Written Opinion of the International Searching Authority," issued in connection with Int'l Appl. No. PCT/US2025/044378, dated Jan. 2, 2026 (18 pages).

"Invitation to Pay Additional Fees of the International Searching Authority," issued in connection with Int'l Appl. No. PCT/US2025/044378, dated Nov. 5, 2025 (2 pages).

"Invitation to Pay Additional Fees of the International Searching Authority," issued in connection with Int'l Appl. No. PCT/US2025/044379, dated Dec. 16, 2025 (3 pages).

Agarwal, P., et al., "Site-specific antibody drug conjugates: the nexus of bioorthogonal chemistry, protein engineering, and drug development.", Bioconjugate chemistry, vol. 26, No. 2, Dec. 12, 2014, pp. 176-192.

Natsume, A., et al., "Improving effector functions of antibodies for cancer treatment: Enhancing ADCC and CDC.", Drug design, development and therapy, Dec. 16, 2008, pp. 7-16.

Nielsen, S. U., et al., "Human T cells resistant to complement lysis by bivalent antibody can be efficiently lysed by dimers of monovalent antibody.", Blood, The Journal of the American Society of Hematology, vol. 100, No. 12, Dec. 1, 2002, pp. 4067-4073.

Chen et al.(Selection and Analysis of an Optimized Anti-VEGF Antibody: Crystal Structure of an Affinity-matured Fab in Complex with Antigen, J. Mol. Biol. (1999) 293, 865+881) (Year: 1999).

US Patent Office "Office Action", issued in connection with U.S. Appl. No. 19/329,322. dated Jan. 13, 2026 (57 pages).

Dondelinger et al., Frontiers in Immunology 9(2278): 1-15 (Year: 2018).

Non-Final Office Action received for U.S. Appl. No. 19/329,322 mailed on Jan. 13, 2026, 57 pages.

* cited by examiner

SEQUENCE LISTING

```
Sequence total quantity: 13
SEQ ID NO: 1              moltype = DNA  length = 369
FEATURE                  Location/Qualifiers
source                   1..369
                         mol_type = other DNA
                         organism = Synthetic construct
```

```
SEQUENCE: 1
caggtacagc tgcagcagtc aggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaagg atcatcccta tccttggtat agcaaactac   180
gcacagaagt tccagggcag agtcacgatt accgcggaca atccacgag cacagcctac    240
atggagctga gcagcctgag atctgaggac acggccgtgt attactgtgc gagaccctcc   300
gaagaggtgg tagctgctta cggtgctttt gatatctggg gccaagggac cacggtcacc   360
gtctcaagc                                                          369

SEQ ID NO: 2              moltype = DNA   length = 336
FEATURE                   Location/Qualifiers
source                    1..336
                          mol_type = other DNA
                          organism = Synthetic construct
SEQUENCE: 2
gaaattgtgc tgactcagtc tccactctcc ctgcccgtca gacctgggga gccggcctcc    60
atctcctgca gggctagtca gagcctcctg cgtagtgacg gattcaacta cttggattgg   120
tacctgcaga agccagggca gtctccacag ctcctggtct atttgggttc taatcggcc    180
tccggggtcc ctgacaggtt cagtggcagt ggatcaggca cagatttac actgaaaatc     240
agcagagtgg aggctgagga tgttggggtt tattactgca tgcaagctgt acaaactccg   300
tacattttg gccaggggac caagctggag atcaaa                             336

SEQ ID NO: 3              moltype = AA   length = 123
FEATURE                   Location/Qualifiers
source                    1..123
                          mol_type = protein
                          organism = Synthetic construct
SEQUENCE: 3
QVQLQQSGAE VKKPGSSVKV SCKASGGTFS SYAISWVRQA PGQGLEWMGR IIPILGIANY    60
AQKFQGRVTI TADKSTSTAY MELSSLRSED TAVYYCARPS EEVVAAYGAF DIWGQGTTVT   120
VSS                                                                123

SEQ ID NO: 4              moltype = AA   length = 112
FEATURE                   Location/Qualifiers
source                    1..112
                          mol_type = protein
                          organism = Synthetic construct
SEQUENCE: 4
EIVLTQSPLS LPVRPGEPAS ISCRASQSLL RSDGFNYLDW YLQKPGQSPQ LLVYLGSNRA    60
SGVPDRFSGS GSGTDFTLKI SRVEAEDVGV YYCMQAVQTP YIFGQGTKLE IK           112

SEQ ID NO: 5              moltype = AA   length = 10
FEATURE                   Location/Qualifiers
source                    1..10
                          mol_type = protein
                          organism = Synthetic construct
SEQUENCE: 5
GGTFSSYAIS                                                           10

SEQ ID NO: 6              moltype = AA   length = 17
FEATURE                   Location/Qualifiers
source                    1..17
                          mol_type = protein
                          organism = Synthetic construct
SEQUENCE: 6
RIIPILGIAN YAQKFQG                                                   17

SEQ ID NO: 7              moltype = AA   length = 16
FEATURE                   Location/Qualifiers
source                    1..16
                          mol_type = protein
                          organism = Synthetic construct
SEQUENCE: 7
ARPSEEVVAA YGAFDI                                                    16

SEQ ID NO: 8              moltype = AA   length = 16
FEATURE                   Location/Qualifiers
source                    1..16
                          mol_type = protein
                          organism = Synthetic construct
SEQUENCE: 8
RASQSLLRSD GFNYLD                                                    16

SEQ ID NO: 9              moltype = AA   length = 7
FEATURE                   Location/Qualifiers
source                    1..7
                          mol_type = protein
                          organism = Synthetic construct
SEQUENCE: 9
```

-continued

```
LGSNRAS                                                                    7

SEQ ID NO: 10          moltype = AA  length = 10
FEATURE                Location/Qualifiers
source                 1..10
                       mol_type = protein
                       organism = Synthetic construct
SEQUENCE: 10
MQAVQTPYIF                                                                 10

SEQ ID NO: 11          moltype = AA  length = 472
FEATURE                Location/Qualifiers
source                 1..472
                       mol_type = protein
                       organism = synthetic construct
SEQUENCE: 11
MDMRVPAQLL GLLLLWLRGA RCQVQLQQSG AEVKKPGSSV KVSCKASGGT FSSYAISWVR  60
QAPGQGLEWM GRIIPILGIA NYAQKFQGRV TITADKSTST AYMELSSLRS EDTAVYYCAR  120
PSEEVVAAYG AFDIWGQGTT VTVSSASTKG PSVFPLAPCS RSTSESTAAL GCLVKDYFPE  180
PVTVSWNSGA LTSGVHTFPA VLQSSGLYSL SSVVTVPSSS LGTKTYTCNV DHKPSNTKVD  240
KRVESKYGPP CPPCPAPEFL GGPSVFLFPP KPKDTLMISR TPEVTCVVVD VSQEDPEVQF  300
NWYVDGVEVH NAKTKPREEQ FNSTYRVVSV LTVLHQDWLN GKEYKCKVSN KGLPSSIEKT  360
ISKAKGQPRE PQVYTLPPSQ EEMTKNQVSL TCLVKGFYPS DIAVEWESNG QPENNYKTTP  420
PVLDSDGSFF LYSRLTVDKS RWQEGNVFSC SVMHEALHNH YTQKSLSLSL GK           472

SEQ ID NO: 12          moltype = AA  length = 241
FEATURE                Location/Qualifiers
source                 1..241
                       mol_type = protein
                       organism = synthetic construct
SEQUENCE: 12
MDMRVPAQLL GLLLLWLRGA RCEIVLTQSP LSLPVRPGEP ASISCRASQS LLRSDGFNYL  60
DWYLQKPGQS PQLLVYLGSN RASGVPDRFS GSGSGTDFTL KISRVEAEDV GVYYCMQAVQ  120
TPYIFGQGTK LEIKRTVAAP SVFIFPPSDE QLKSGTASVV CLLNNFYPRE AKVQWKVDNA  180
LQSGNSQESV TEQDSKDSTY SLSSTLTLSK ADYEKHKVYA CEVTHQGLSS PVTKSFNRGE  240
C                                                                          241

SEQ ID NO: 13          moltype = AA  length = 22
FEATURE                Location/Qualifiers
source                 1..22
                       mol_type = protein
                       organism = synthetic construct
SEQUENCE: 13
MDMRVPAQLL GLLLLWLRGA RC                                                    22
```

NUCLEIC ACIDS, VECTORS, AND CELLS THAT ENCODE ANTI-Sp17 ANTIBODIES AND OTHER Sp17 BINDING PROTEINS

CROSS-REFERENCE TO RELATED APPLICATIONS

This application claims the benefit of U.S. Provisional Patent Application No. 63/524,806, filed Jul. 3, 2023, the disclosure of which is incorporated, in its entirety, by this reference.

SEQUENCE LISTING

This disclosure includes a sequence listing, which has file name "Sequence_Listing_1200590011.xml," which was created on Jan. 9, 2024, which has a file size of 14,063 bytes, and which is incorporated by reference in its entirety.

FIELD OF THE INVENTION

The present invention relates to proteins that bind sperm protein 17 (Sp17), which Sp17-binding proteins are derived from an anti-Sp17 Fab and include anti-Sp17 monoclonal antibodies as well as Sp17-binding conjugates and fusion proteins derived from the complementarity determining regions (CDRs) of the Fab. The present invention specifically relates to the use of Sp17-binding proteins in the diagnosis and treatment of various health conditions including cancer.

BACKGROUND OF SOME ASPECTS OF THE SPECIFICATION

The human Sp17 gene, which is located on chromosome 11q24.2, encodes a highly-conserved, antigenic, 17.4 kilo-dalton protein Sp17 that is expressed in spermatozoa. The Sp17 protein is involved in acrosome reactions during fertilization. Immunohistochemistry on tissue microarrays and Reverse Transcription-Polymerase Chain Reactions (RT-PCRs) on a panel of RNA from different tissues suggests that Sp17 is expressed in normal testes and absent in other healthy tissues. Sp17 was also identified as an aberrantly expressed tumor antigen in multiple myeloma, lymphoma, ovarian cancer, and non-small cell lung cancer.

SUMMARY OF SOME ASPECTS OF THE SPECIFICATION

Various aspects of this disclosure relate to the discovery of a novel anti-Sp17 Fab that includes CDRs that have nanomolar affinity for Sp17 and high specificity for Sp17 relative to other human proteins. The CDRs retain their high affinity and fidelity in various antibody formats. A human antibody comprising the CDRs is in pre-clinical development for use as a cancer immunotherapeutic. The CDRs are also compatible with a full range of immunotherapeutic strategies including antibody conjugates, bi-specific proteins (for example, as T-cell engagers), and adoptive cell therapies (for example, as CAR-Ts). The CDRs may also be cloned into antibodies for laboratory research and diagnostics. The following disclosure describes, for example, a chimeric IgG comprising a mouse Fc region that may be used in various assays and diagnostics in combination with an anti-mouse secondary antibody. This disclosure describes its use with flow cytometry, immunohistochemistry, and western blotting.

The preceding Background and Summary sections are provided as a brief introduction to the described subject matter as well as a synopsis of some of the technological improvements and advantages that it provides. The Background and Summary shall not be construed as identifying essential aspects of the described subject matter, nor shall they be construed to limit the interpretation of this specification or any patent claim that matures from this specification.

BRIEF DESCRIPTION OF THE DRAWINGS

A further understanding of this specification may be appreciated with reference to the following drawings. The drawings are exemplary, and neither this specification nor any patent claim that matures from this specification shall be construed as limited by the drawings.

DETAILED DESCRIPTION

Figure 1:
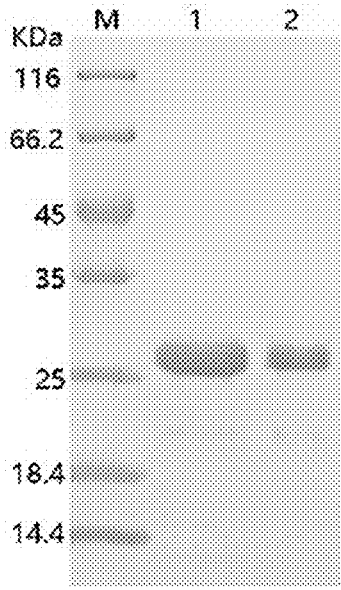
FIG. 1 is an image of an SDS-PAGE gel loaded with a molecular weight standard (lane M) and 2 micrograms of recombinant Sp17 protein under reducing conditions (lane 1) and non-reducing conditions (lane 2).

Various aspects of this disclosure relate to antibodies that display high-affinity for human Sp17 protein. These antibodies were developed using a Fab phage-display biopanning strategy on a library generated from the peripheral blood of 120 healthy donors as set forth in Example 1 below. The library included about a trillion different combinations. The best-performing Fab in the library had an immunoglobulin heavy chain variable region (VH) with the nucleotide sequence set forth in SEQ ID NO: 1 and an immunoglobulin light chain variable region (VL) with the nucleotide sequence set forth in SEQ ID NO: 2, which nucleotide sequences are depicted in Table 1 below. The VH amino acid sequence is set forth in SEQ ID NO: 3, and the VL amino acid sequence is set forth in SEQ ID NO: 4. The VH and VL amino acid sequences are depicted in Table 2 below, in which CDRs are depicted with bold and underline, and in which framework regions are depicted with plain text. CDR sequences are set forth in SEQ ID NO: 5-10 and are independently depicted in Table 3 below. One of ordinary skill will recognize that the precise demarcation between CDR and framework regions is blurred at least for some of the CDRs, and the CDRs as set forth in Tables 2 & 3 and in SEQ ID NO: 5-10 may therefore include one or more amino acids that might be more-appropriately classified as framework rather than CDR.

Nucleotide sequences encoding the variable regions of the best-performing Fab (SEQ ID NO: 1 & 2) were initially cloned into a mouse IgG2a heavy chain gene and a mouse kappa light chain gene to express a chimeric monoclonal antibody (chAB2). The affinity of the chimeric antibody was determined to be about 2 nanomolar by surface plasmon resonance. Immunohistochemical analysis of the chimeric antibody against 33 normal human tissues indicated that the variable regions lack detectable cross-reactivity. The chimeric antibody is therefore useful, for example, for laboratory analyses including immunohistochemistry, western blotting, and flow cytometry, as described below, as well as for medical diagnostics including enzyme-linked immunosorbent assays (ELISA).

Various aspects of this disclosure relate to a kit, comprising a recombinant anti-Sp17 antibody as described anywhere in this disclosure and a reporter, wherein the kit is configured to detect Sp17 in a biological sample. In some embodiments, the reporter comprises either (i) a conjugated dye or (ii) a conjugated fluorescent, phosphorescent, chemiluminescent, radioactive, or magnetic label. In some specific embodiments, the reporter comprises a secondary antibody; the conjugated dye is an antibody-conjugated dye; and the conjugated fluorescent, phosphorescent, chemiluminescent, radioactive, or magnetic label is an antibody-conjugated fluorescent, phosphorescent, chemiluminescent, radioactive, or magnetic label. In some very specific embodiments, the kit is configured to detect Sp17 in the biological sample by immunohistochemistry, western blotting, flow cytometry, magnetic-activated cell sorting, ELISA, or chemiluminescent immunoassay.

The human variable regions were then cloned into a human IgG4 heavy chain gene and a human kappa light chain gene to produce a human monoclonal antibody (SP17-AB2) suitable for use as a therapeutic antibody. The heavy chain constant region was mutated to include a Ser228Pro mutation to reduce non-specific interactions with Fc receptor gamma (FcTR). The full heavy chain has the amino acid sequence set forth in SEQ ID NO: 10, and the full light chain has the amino acid sequence set forth in SEQ ID NO: 11, which are depicted in Table 4 below.

Various aspects of this disclosure relate to a recombinant anti-Sp17 antibody or antigen-binding fragment thereof, which comprises the CDRs described above or which comprises sequence homology (or sequence identity) with the VH and VL variable regions that comprise the CDRs as described above. In all embodiments, the antibody or antigen-binding fragment thereof binds human Sp17.

The term "antibody" includes immunoglobulins (Ig's) of different classes (for example, IgA, IgG, IgM, IgD, and IgE) and subclasses (for example, IgG2a and IgG4) and also includes fully-human antibodies, chimeric antibodies, and engineered variants thereof. This specification describes, for example, a chimeric human-mouse antibody (chAB2) as well as a fully-human antibody (SP17-AB2) that has been engineered to contain a Ser228Pro mutation.

The term "antigen-binding fragment" refers to both Fab fragments and single-chain variable fragments (ScFv). scFvs are fusion proteins of two variable regions connected with a flexible linker, which fusion proteins retain antigen-binding properties comparable to a Fab. Examples of scFvs include brolucizumab (also known as BEOVU®).

As used in this disclosure, the term "sequence homology" refers to percent "positives" as determined by Standard Protein BLAST® over the full length of a sequence set forth in a SEQ ID NO. Standard Protein BLAST® is available at https://blast.ncbi.nlm.nih.gov/Blast.cgi?PROGRAM=blastp. BLAST® is generally described in Altschul, et al. (1997), "Gapped BLAST and PSI-BLAST: a new generation of protein database search programs", Nucleic Acids Res. 25:3389-3402, and in Altschul, et al. (2005) "Protein database searches using compositionally adjusted substitution matrices", FEBS J. 272: 5101-5109. As used in this disclosure, the term "sequence identity" refers to the percent of exact matches over the full length of a sequence set forth in a SEQ ID NO.

In all embodiments, the recombinant anti-Sp17 antibody or antigen-binding fragment thereof comprises two variable domains. The two variable domains include a heavy chain variable region and a light chain variable region. In some specific embodiments, the heavy chain variable region has a percent sequence homology (or sequence identity) with SEQ ID NO: 5, 6, and 7, and the light chain variable region has a percent sequence homology (or sequence identity) with SEQ ID NO: 8, 9, and 10. In some very specific embodiments, the heavy chain variable region has a percent sequence homology (or sequence identity) with SEQ ID NO:

3, and the light chain variable region has a percent sequence homology (or sequence identity) with SEQ ID NO: 4.

In some embodiments, the antibody or antigen-binding fragment thereof comprises (1) a first variable domain that comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; and (2) a second variable domain that comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10.

In some embodiments, the recombinant anti-Sp17 antibody comprises four variable domains, wherein the antibody comprises (1) a third variable domain that comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; and (2) a fourth variable domain that comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10. Such antibodies include, for example, IgG antibodies.

In some embodiments, one or more of VH CDR1, VH CDR2, VH CDR3, VL CDR1, VL CDR2, and VL CDR3 comprise one or more conservative mutations. Conservative mutations are known in the art and include, for example, threonine to serine, isoleucine to valine or leucine, tyrosine to phenylalanine, aspartate to glutamate, asparagine to glutamine, arginine to lysine, and like substitutions. In this disclosure, a conservative mutation is a "positive" match in Standard Protein BLAST® that is not an identity.

Various aspects of this disclosure relate to a recombinant anti-Sp17 antibody or antigen-binding fragment thereof, comprising two variable domains, wherein: the antibody or antigen-binding fragment thereof comprises a first variable domain that comprises an amino acid sequence that has at least 90 percent sequence homology with SEQ ID NO: 3; the antibody or antigen-binding fragment thereof comprises a second variable domain that comprises an amino acid sequence that has at least 90 percent sequence homology with SEQ ID NO: 4; and the antibody or antigen-binding fragment thereof binds human Sp17. In some specific embodiments, the first variable domain comprises an amino acid sequence that has at least 90 percent sequence identity with SEQ ID NO: 3; the second variable domain comprises an amino acid sequence that has at least 90 percent sequence identity with SEQ ID NO: 4; and the antibody or antigen-binding fragment thereof binds human Sp17.

SEQ ID NO: 3 is the VH amino acid sequence, which includes VH CDR1, VH CDR2, VH CDR3, and framework regions. In some embodiments, the VH amino acid sequence comprises mutations relative to SEQ ID NO: 3 such that the VH amino acid sequence has at least 90 percent sequence homology with SEQ ID NO: 3 but less than 100 percent sequence homology. In some specific embodiments, the VH amino acid sequence comprises mutations relative to SEQ ID NO: 3 such that the VH amino acid sequence has at least 90 percent sequence identity with SEQ ID NO: 3 but less than 100 percent sequence identity.

SEQ ID NO: 4 is the VL amino acid sequence, which includes VL CDR1, VL CDR2, VL CDR3, and framework regions. In some embodiments, the VL amino acid sequence comprises mutations relative to SEQ ID NO: 4 such that the VL amino acid sequence has at least 90 percent sequence homology with SEQ ID NO: 4 but less than 100 percent sequence homology. In some specific embodiments, the VL amino acid sequence comprises mutations relative to SEQ ID NO: 4 such that the VL amino acid sequence has at least 90 percent sequence identity with SEQ ID NO: 4 but less than 100 percent sequence identity.

Mutations to the VH and/or VL amino acid sequences may be engineered, for example, to tune the avidity of an antibody (or antigen-binding fragment thereof) to the Sp17 antigen, to modulate expression or glycosylation, and/or for other purposes.

In some embodiments, the first variable domain comprises an amino acid sequence that has at least 95 percent sequence homology with SEQ ID NO: 3. In some specific embodiments, the first variable domain comprises an amino acid sequence that has at least 97 percent sequence homology with SEQ ID NO: 3. In some even more specific embodiments, the first variable domain comprises an amino acid sequence that has at least 98 percent sequence homology with SEQ ID NO: 3. In some very specific embodiments, the first variable domain comprises an amino acid sequence that has at least 99 percent sequence homology with SEQ ID NO: 3.

In some embodiments, the first variable domain comprises an amino acid sequence that has at least 95 percent sequence identity with SEQ ID NO: 3. In some specific embodiments, the first variable domain comprises an amino acid sequence that has at least 97 percent sequence identity with SEQ ID NO: 3. In some even more specific embodiments, the first variable domain comprises an amino acid sequence that has at least 98 percent sequence identity with SEQ ID NO: 3. In some very specific embodiments, the first variable domain comprises an amino acid sequence that has at least 99 percent sequence identity with SEQ ID NO: 3.

In some embodiments, the second variable domain comprises an amino acid sequence that has at least 95 percent sequence homology with SEQ ID NO: 4. In some specific embodiments, the second variable domain comprises an amino acid sequence that has at least 97 percent sequence homology with SEQ ID NO: 4. In some even more specific embodiments, the second variable domain comprises an amino acid sequence that has at least 98 percent sequence homology with SEQ ID NO: 4. In some very specific embodiments, the second variable domain comprises an amino acid sequence that has at least 99 percent sequence homology with SEQ ID NO: 4.

In some embodiments, the second variable domain comprises an amino acid sequence that has at least 95 percent sequence identity with SEQ ID NO: 4. In some specific embodiments, the second variable domain comprises an amino acid sequence that has at least 97 percent sequence identity with SEQ ID NO: 4. In some even more specific embodiments, the second variable domain comprises an amino acid sequence that has at least 98 percent sequence identity with SEQ ID NO: 4. In some very specific embodiments, the second variable domain comprises an amino acid sequence that has at least 99 percent sequence identity with SEQ ID NO: 4.

In some embodiments, the recombinant anti-Sp17 antibody comprises four variable domains, wherein the antibody comprises (1) a third variable domain that comprises an amino acid sequence that has at least 90 percent sequence homology with SEQ ID NO: 3 (such as at least 95, 97, 98, or 99 percent sequence homology); and (2) a fourth variable domain that comprises an amino acid sequence that has at least 90 percent sequence homology with SEQ ID NO: 4 (such as at least 95, 97, 98, or 99 percent sequence homology). In some specific embodiments, the third variable domain comprises an amino acid sequence that has at least 90 percent sequence identity with SEQ ID NO: 3 (such as at least 95, 97, 98, or 99 percent sequence homology), and the fourth variable domain comprises an amino acid sequence that has at least 90 percent sequence identity with SEQ ID NO: 4 (such as at least 95, 97, 98, or 99 percent sequence identity).

In some embodiments, the recombinant anti-Sp17 antibody or antigen-binding fragment thereof has a KD with human Sp17 of no greater than 25 nanomolar. In some specific embodiments, the recombinant anti-Sp17 antibody or antigen-binding fragment thereof has a KD with human Sp17 of no greater than 10 nanomolar. In some very specific embodiments, the recombinant anti-Sp17 antibody or antigen-binding fragment thereof has a KD with human Sp17 of no greater than 2.5 nanomolar.

In some embodiments, KD is determined by surface plasmon resonance (such as with a Biacore™ instrument).

In some embodiments, the recombinant anti-Sp17 antibody comprises an IgG heavy chain constant region. In some specific embodiments, the recombinant anti-Sp17 antibody comprises an IgG2 heavy chain constant region. In some specific embodiments, the recombinant anti-Sp17 antibody comprises an IgG4 heavy chain constant region. In some very specific embodiments, the recombinant anti-Sp17 antibody comprises an IgG2a heavy chain constant region.

In some embodiments, the recombinant anti-Sp17 antibody comprises a kappa or lambda light chain constant region. In some specific embodiments, the recombinant anti-Sp17 antibody comprises a kappa light chain constant region.

In some embodiments, the recombinant anti-Sp17 antibody comprises a mouse heavy chain constant region and a mouse light chain constant region. In some specific embodiments, the recombinant anti-Sp17 antibody comprises a mouse IgG heavy chain constant region and a mouse kappa or lambda light chain constant region. In some very specific embodiments, the recombinant anti-Sp17 antibody comprises a mouse IgG2a heavy chain constant region and a mouse kappa light chain constant region.

In some embodiments, the recombinant anti-Sp17 antibody comprises a human heavy chain constant region and a human light chain constant region. In some specific embodiments, the recombinant anti-Sp17 antibody comprises a human IgG heavy chain constant region and a human kappa or lambda light chain constant region. In some very specific embodiments, the recombinant anti-Sp17 antibody comprises a human IgG4 heavy chain constant region and a human kappa light chain constant region.

In some embodiments, the recombinant anti-Sp17 antibody has a heavy chain that has at least 90 percent sequence homology with SEQ ID NO: 11. In some specific embodiments, the recombinant anti-Sp17 antibody has a heavy chain that has at least 95 percent sequence homology with SEQ ID NO: 11. In some even more specific embodiments, the recombinant anti-Sp17 antibody has a heavy chain that has at least 98 percent sequence homology with SEQ ID NO: 11. In some very specific embodiments, the recombinant anti-Sp17 antibody has a heavy chain that has at least 99 percent sequence homology with SEQ ID NO: 11.

In some embodiments, the recombinant anti-Sp17 antibody has a heavy chain that has at least 90 percent sequence identity with SEQ ID NO: 11. In some specific embodiments, the recombinant anti-Sp17 antibody has a heavy chain that has at least 95 percent sequence identity with SEQ ID NO: 11. In some even more specific embodiments, the recombinant anti-Sp17 antibody has a heavy chain that has at least 98 percent sequence identity with SEQ ID NO: 11. In some very specific embodiments, the recombinant anti-Sp17 antibody has a heavy chain that has at least 99 percent sequence identity with SEQ ID NO: 11.

In some embodiments, the recombinant anti-Sp17 antibody has a light chain that has at least 90 percent sequence homology with SEQ ID NO: 12. In some specific embodiments, the recombinant anti-Sp17 antibody has a light chain that has at least 95 percent sequence homology with SEQ ID NO: 12. In some even more specific embodiments, the recombinant anti-Sp17 antibody has a light chain that has at least 98 percent sequence homology with SEQ ID NO: 12. In some very specific embodiments, the recombinant anti-Sp17 antibody has a light chain that has at least 99 percent sequence homology with SEQ ID NO: 12.

In some embodiments, the recombinant anti-Sp17 antibody has a light chain that has at least 90 percent sequence identity with SEQ ID NO: 12. In some specific embodiments, the recombinant anti-Sp17 antibody has a light chain that has at least 95 percent sequence identity with SEQ ID NO: 12. In some even more specific embodiments, the recombinant anti-Sp17 antibody has a light chain that has at least 98 percent sequence identity with SEQ ID NO: 12. In some very specific embodiments, the recombinant anti-Sp17 antibody has a light chain that has at least 99 percent sequence identity with SEQ ID NO: 12.

In some embodiments, the recombinant anti-Sp17 antibody has (1) a heavy chain that has at least 90 percent sequence homology with SEQ ID NO: 11, and (2) a light chain that has at least 90 percent sequence homology with SEQ ID NO: 12. In some specific embodiments, the recombinant anti-Sp17 antibody has (1) a heavy chain that has at least 95 percent sequence homology with SEQ ID NO: 11, and (2) a light chain that has at least 95 percent sequence homology with SEQ ID NO: 12. In some even more specific embodiments, the recombinant anti-Sp17 antibody has (1) a heavy chain that has at least 98 percent sequence homology with SEQ ID NO: 11, and (2) a light chain that has at least 98 percent sequence homology with SEQ ID NO: 12. In some very specific embodiments, the recombinant anti-Sp17 antibody has (1) a heavy chain that has at least 99 percent sequence homology with SEQ ID NO: 11, and (2) a light chain that has at least 99 percent sequence homology with SEQ ID NO: 12.

In some embodiments, the recombinant anti-Sp17 antibody has (1) a heavy chain that has at least 90 percent sequence identity with SEQ ID NO: 11, and (2) a light chain that has at least 90 percent sequence identity with SEQ ID NO: 12. In some specific embodiments, the recombinant anti-Sp17 antibody has (1) a heavy chain that has at least 95 percent sequence identity with SEQ ID NO: 11, and (2) a light chain that has at least 95 percent sequence identity with SEQ ID NO: 12. In some even more specific embodiments, the recombinant anti-Sp17 antibody has (1) a heavy chain that has at least 98 percent sequence identity with SEQ ID NO: 11, and (2) a light chain that has at least 98 percent sequence identity with SEQ ID NO: 12. In some very specific embodiments, the recombinant anti-Sp17 antibody has (1) a heavy chain that has at least 99 percent sequence identity with SEQ ID NO: 11, and (2) a light chain that has at least 99 percent sequence identity with SEQ ID NO: 12.

In some embodiments, the recombinant anti-Sp17 antibody comprises two heavy chains and two light chains, wherein each of the two heavy chains has at least 90 percent sequence homology with SEQ ID NO: 11, and each of the two light chains has at least 90 percent sequence homology with SEQ ID NO: 12. In some specific embodiments, the recombinant anti-Sp17 antibody comprises two heavy chains and two light chains, wherein each of the two heavy chains has at least 95 percent sequence homology with SEQ ID NO: 11, and each of the two light chains has at least 95 percent sequence homology with SEQ ID NO: 12. In some even more specific embodiments, the recombinant anti-Sp17 antibody comprises two heavy chains and two light chains, wherein each of the two heavy chains has at least 98 percent sequence homology with SEQ ID NO: 11, and each of the two light chains has at least 98 percent sequence homology with SEQ ID NO: 12. In some very specific embodiments, the recombinant anti-Sp17 antibody comprises two heavy chains and two light chains, wherein each of the two heavy chains has at least 99 percent sequence homology with SEQ ID NO: 11, and each of the two light chains has at least 99 percent sequence homology with SEQ ID NO: 12. Such antibodies include, for example, IgG antibodies.

In some embodiments, the recombinant anti-Sp17 antibody comprises two heavy chains and two light chains, wherein each of the two heavy chains has at least 90 percent sequence identity with SEQ ID NO: 11, and each of the two light chains has at least 90 percent sequence identity with SEQ ID NO: 12. In some specific embodiments, the recombinant anti-Sp17 antibody comprises two heavy chains and two light chains, wherein each of the two heavy chains has at least 95 percent sequence identity with SEQ ID NO: 11, and each of the two light chains has at least 95 percent sequence identity with SEQ ID NO: 12. In some even more specific embodiments, the recombinant anti-Sp17 antibody comprises two heavy chains and two light chains, wherein each of the two heavy chains has at least 98 percent sequence identity with SEQ ID NO: 11, and each of the two light chains has at least 98 percent sequence identity with SEQ ID NO: 12. In some very specific embodiments, the recombinant anti-Sp17 antibody comprises two heavy chains and two light chains, wherein each of the two heavy chains has at least 99 percent sequence identity with SEQ ID NO: 11, and each of the two light chains has at least 99 percent sequence identity with SEQ ID NO: 12. Such antibodies include, for example, IgG antibodies.

In some embodiments, the recombinant anti-Sp17 antibody comprises at least four variable domains, wherein: the first and second variable domains are paired in the antibody such that the first and second variable domains bind an epitope of human Sp17, and the antibody comprises a third variable domain and a fourth variable domain that are paired in the antibody such that the third and fourth variable domains bind a different epitope. Such antibodies include, for example, IgG-like bispecific antibodies such as trifunctional antibodies. The different epitope may be, for example, a CD3 epitope, and the antibody may function as a therapeutic antibody by crosslinking a cancer cell that expresses Sp17 with a T-cell that expresses CD3 and a leukocyte that expresses an Fc receptor (such as a monocyte, macrophage, natural killer cell, or dendritic cell), which binds to an Fc region of the antibody. Examples of trivalent antibodies include catumaxomab (also known as REMOVAB®), which binds the EpCAM cancer antigen, CD3, and Fc receptor (see, for example, U.S. Pat. No. 8,277,806, which is incorporated by reference in its entirety). Those of ordinary skill are capable of designing trivalent antibodies that bind Sp17, CD3, and Fc receptor, for example, by replacing the catumaxomab variable regions that bind EpCAM with the variable regions set forth in SEQ ID NOs: 3 & 4. Other trivalent antibodies that bind Sp17 can be similarly engineered based on SEQ ID NOs: 3 & 4 and the known sequences of other existing trivalent antibodies. In some specific embodiments, the recombinant anti-Sp17 antibody comprises an Fc region. In some specific embodiments, the different epitope is an extracellular epitope of CD3. In some very specific embodiments, the recombinant anti-Sp17 antibody comprises an Fc region, and the different epitope is an extracellular epitope of CD3.

In this disclosure, the term "paired" refers a spatial proximity and orientation between VH and VL regions that allow the VH and VL regions to simultaneously bind an epitope. VH and VL regions may be paired, for example, in a Fab by quaternary structure that includes one or more disulfide bonds and non-covalent interactions between the heavy chain constant domain CHi and the light chain constant domain CL. VH and VL regions may also be paired, for example, as a scFv fusion protein, which generally includes a flexible linker, such as polyglycine, that tethers the VH and VL regions in spatial proximity and permits spatial orientations in which the VH and VL regions can simultaneously bind an epitope.

Various aspects of this disclosure relate to an antibody conjugate comprising a recombinant anti-Sp17 antibody as described anywhere in this disclosure, wherein the recombinant anti-Sp17 antibody is conjugated to a radioactive isotope or a pharmaceutical agent.

In some embodiments, the recombinant anti-Sp17 antibody is conjugated to a radioactive isotope. In some specific embodiments, the recombinant anti-Sp17 antibody is conjugated to a radioactive isotope selected from actinium-225, astatine-211, bismuth-212, bismuth-213, copper-67, gallium-68, holmium-166, iodine-124, iodine-131, lutetium-177, samarium-153, technetium-99, terbium-149, and yttrium-90. Examples of antibodies conjugated to radioactive isotopes include tositumomab (also known as BEXXAR®) and ibritumomab tiuxetan (also known as ZEVALIN®). Those of ordinary skill are capable of designing antibodies that are conjugated to radioactive isotopes using known strategies such as those used to conjugate iodine-131 in tositumomab and to conjugate yttrium-90 or indium-111 to ibritumomab (see, for example, U.S. Pat. No. 6,565,827 & 7,422,739, which are incorporated by reference in their entirety).

In some embodiments, the recombinant anti-Sp17 antibody is conjugated to a pharmaceutical agent. In some specific embodiments, the recombinant anti-Sp17 antibody is conjugated to a moiety selected from calicheamicin, camptothecin, deruxtecan, doxorubicin, emtansine, exatecan, irinotecan, maleimidocaproyl monomethyl auristatin F, mertansine, monomethyl auristatin F, paclitaxel, PE38, pyr-
rolobenzodiazepine, SN-38, and vedotin. Examples of anti-
bodies conjugated to pharmaceutical agents include
gemtuzumab ozogamicin (also known as MYLOTARG®)
and trastuzumab emtansine (also known as KADCYLA®).
Those of ordinary skill are capable of designing antibodies
that are conjugated to pharmaceutical agents using known
strategies such as those used to conjugate calicheamicin to
gemtuzumab and emtansine to trastuzumab (see, for
example, U.S. Pat. No. 5,877,296 & 8,088,387, which are
incorporated by reference in their entirety).

Various aspects of this disclosure relate to a pharmaceu-
tical composition comprising a recombinant anti-Sp17 anti-
body, an antigen-binding fragment thereof, or a conjugate
thereof as described anywhere in this disclosure and a
pharmaceutically acceptable carrier. Suitable pharmaceuti-
cally acceptable carriers generally include water with dis-
solved solutes that buffer pH and provide metal cations and
an ionic strength that stabilize an antibody or other thera-
peutic of this disclosure. Such formulations are generally
sterile, and the selection and preparation of such pharma-
ceutically acceptable carriers are well known. Solid formats
including lyophilized therapeutics generally include, for
example, metal cations, anions, and optionally polyols such
as sugars (for example, trehalose or glucose) that stabilize
the therapeutic in the solid phase and during its reconstitu-
tion into an aqueous format. General guidance on selecting
pharmaceutically acceptable carriers is available, for
example, in REMINGTON: THE SCIENCE AND PRACTICE OF PHAR-
MACY, 22nd edition (Allen Jr, Loyd V., editor) Pharmaceu-
tical Press, 2012, and the skilled practitioner will also look
to the formulations of the therapeutics described in this
disclosure as well as other existing therapeutics in selecting
a pharmaceutically acceptable carrier. Such guidance is
generally available in the scientific literature and on existing
product labels.

In some embodiments, the pharmaceutical composition is
suitable for administration to a subject. In some specific
embodiments, the pharmaceutical composition is suitable
for administration to a human patient. In some very specific
embodiments, the pharmaceutical composition is suitable
for intravenous administration to a human patient.

In some embodiments, the pharmaceutical composition
comprises an anti-Sp17 antibody, and the antibody has a
purity of at least 85 percent relative to total protein in the
pharmaceutical composition. In some specific embodiments,
the pharmaceutical composition comprises an anti-Sp17
antibody, and the antibody has a purity of at least 90 percent
relative to total protein in the pharmaceutical composition.
In some very specific embodiments, the pharmaceutical
composition comprises an anti-Sp17 antibody, and the anti-
body has a purity of at least 93 percent relative to total
protein in the pharmaceutical composition.

In some embodiments, purity is determined by chroma-
tography. In some specific embodiments, purity is deter-
mined by HPLC.

Various aspects of this disclosure relate to a kit, compris-
ing (1) a hermetically-sealed container that contains the
pharmaceutical composition as described anywhere in this
specification and (2) instructions for use of the pharmaceu-
tical composition.

Various aspects of this disclosure relate to a medical
device, comprising the pharmaceutical composition as
described anywhere in this specification. In some embodi-
ments, the medical device is a syringe, a venous cannula, or
a drug-eluting implant.

Various aspects of this disclosure relate to a method of
treating or preventing cancer in a subject, comprising iden-
tifying that the subject comprises cells that ectopically
express Sp17 and administering a pharmaceutical composi-
tion as described anywhere in this disclosure. Determining
that the subject comprises cells that ectopically express Sp17
include, for example, identifying mRNA that encodes Sp17
by RT-PCR and identifying Sp17 protein expression by flow
cytometry and/or immunohistochemistry. Such methods
may advantageously allow determination that a cancer cell
ectopically expresses Sp17, for example, based upon the
prior selection of one or more cancer cells for analysis or
based upon the co-identification of ectopic Sp17 expression
and a cancer phenotype such as the co-expression of Sp17
and another cancer antigen.

Various aspects of this disclosure relate to a method to
modulate cells that express Sp17 in a human subject, com-
prising administering the immunotherapeutic agent to the
human subject, wherein the immunotherapeutic agent is or
comprises a recombinant anti-Sp17 antibody or antigen-
binding fragment thereof as described anywhere in this
disclosure. In some embodiments, the method is a method of
treating or preventing cancer in a human subject. In some
specific embodiments, the method is a method of treating or
preventing cancer in a human subject, the human subject
presents with cancer, and at least a portion of the cells that
express Sp17 are cancer cells.

In some embodiments the immunotherapeutic agent is
administered at an effective amount that is effective to
induce cell death in at least a portion of the cells that express
Sp17, and the method modulates the cells that express Sp17
by inducing cell death. In some specific embodiments, the
immunotherapeutic agent comprises an Fc region, and the
method induces cell death by Fc receptor mediated binding
and activation of one or more leukocytes to the cells that
express Sp17. In some specific embodiments, the immuno-
therapeutic agent is conjugated to a radioactive isotope, and
the method induces cell death by emitting radiation within or
in proximity to the cells that express Sp17. In some specific
embodiments, the immunotherapeutic agent is conjugated to
a pharmaceutical agent, the pharmaceutical agent is cyto-
toxic, and the method induces cell death by releasing the
pharmaceutical agent within or in proximity to the cells that
express Sp17. In some very specific embodiments, the
immunotherapeutic agent is conjugated to a pharmaceutical
agent by a labile linker, the pharmaceutical agent is cyto-
toxic, and the method induces cell death by releasing the
pharmaceutical agent within or in proximity to the cells that
express Sp17.

In some embodiments, the subject is a mammal. In some
specific embodiments, the subject is a rodent, lagomorph,
feline, canine, porcine, ovine, caprine, *lama*, bovine, equine,
or primate. In some very specific embodiments, the subject
is a human patient.

In some embodiments, the subject is male or female. In
some specific embodiments, the subject is female. In some
specific embodiments, the subject is male.

In some embodiments, the subject presents with ectopic
expression of Sp17. In some specific embodiments, the
subject presents with cancer, and cells of the cancer ectopi-
cally express Sp17.

In some embodiments, the method comprises identifying
that the subject comprises cells that ectopically express
Sp17.

In some embodiments, the method comprises identifying
that the subject comprises cells that ectopically express
Sp17, wherein the cells that ectopically express Sp17 comprise leukocytes, and the cancer is a lymphoma, leukemia, or myeloma. In some specific embodiments, the method comprises identifying that the subject comprises cells that ectopically express Sp17, wherein the cells that ectopically express Sp17 comprise plasma cells, and the cancer is multiple myeloma. In some specific embodiments, the method comprises identifying that the subject comprises cells that ectopically express Sp17, wherein the cells that ectopically express Sp17 comprise lymphocytes, and the cancer is lymphoma. In some specific embodiments, the method comprises identifying that the subject comprises cells that ectopically express Sp17, wherein the cells that ectopically express Sp17 comprise ovarian cells, and the cancer is ovarian cancer. In some specific embodiments, the method comprises identifying that the subject comprises cells that ectopically express Sp17, wherein the cells that ectopically express Sp17 comprise lung epithelial cells, and the cancer is non-small cell lung cancer.

In some embodiments, the method comprises identifying that a tissue sample of the human subject comprises either RNA encoding Sp17 or Sp17 protein prior to the administering.

In some embodiments, the tissue sample is a blood sample.

In some embodiments, the tissue sample is a biopsy. In some specific embodiments, the tissue sample is a tumor biopsy. In some very specific embodiments, the tissue sample is a bone marrow biopsy. In some very specific embodiments, the tissue sample is an ovarian biopsy. In some very specific embodiments, the tissue sample is a lung biopsy.

In some embodiments, the method comprises identifying that the tissue sample comprises a cancer biomarker, wherein the cancer biomarker is neither RNA encoding Sp17 nor Sp17 protein.

In some embodiments, the method lacks identifying that the cancer biomarker and the RNA encoding Sp17 are co-expressed or co-localized, and/or the method lacks identifying that the cancer biomarker and the Sp17 protein are co-expressed or co-localized. Sp17 is unique because healthy females are not known to express Sp17 and because healthy males are only known to express Sp17 in testes tissue. The detection of Sp17 RNA or Sp17 protein in a biological sample other than a testes sample therefore suggests the existence of a cancer-related phenotype that is treatable with the immunotherapeutic agents of this disclosure even in the absence of data to suggest that Sp17 is expressed on cells that have a cancer-related phenotype such as by detecting the expression of Sp17 on a cell that displays a cancer morphology or by detecting the co-expression or co-localization of Sp17 and a cancer biomarker.

In some embodiments, identifying that the tissue sample comprises RNA encoding Sp17 comprises RT-PCR. In some specific embodiments, identifying that the tissue sample comprises RNA encoding Sp17 comprises RT-PCR, and the RT-PCR does not distinguish cancer cells that comprise RNA encoding Sp17 from healthy cells.

In some embodiments, identifying that the tissue sample comprises Sp17 protein comprises ELISA. In some specific embodiments, identifying that the tissue sample comprises Sp17 protein comprises ELISA, and the ELISA does not distinguish cancer cells that comprise RNA encoding Sp17 from healthy cells.

In some embodiments, the cells that ectopically express Sp17 comprise leukocytes, and the cancer is a lymphoma, leukemia, or myeloma. In some specific embodiments, the cells that ectopically express Sp17 comprise leukocytes, and the cancer is multiple myeloma or lymphoma. In some very specific embodiments, the cells that ectopically express Sp17 comprise plasma cells, and the cancer is multiple myeloma. In some very specific embodiments, the cells that ectopically express Sp17 comprise lymphocytes, and the cancer is lymphoma.

In some embodiments, the cells that ectopically express Sp17 comprise ovarian cells, and the cancer is ovarian cancer.

In some embodiments, the cells that ectopically express Sp17 comprise lung epithelial cells, and the cancer is non-small cell lung cancer.

In some embodiments, the administering is selected from intravenous, intramuscular, subcutaneous, intradermal, intraocular, parenteral, intraperitoneal, intrathecal, intralesional, and intratumoral administration. In some specific embodiments, the administering is intravenous administration.

Various aspects of this disclosure relate to a recombinant nucleic acid encoding a recombinant anti-Sp17 antibody or antigen-binding fragment thereof as described anywhere in this disclosure.

Various aspects of this disclosure relate to a recombinant nucleic acid, comprising a nucleotide sequence that encodes a protein that comprises an antigen-binding region, wherein (1) the antigen-binding region comprises a first variable domain and a second variable domain; (2) the first variable domain comprises a VH CDR1 region comprising an amino acid sequence that is identical to at least 7, 8, 9, or 10 consecutive amino acids set forth in SEQ ID NO: 5, a VH CDR2 region comprising an amino acid sequence that is identical to at least 7, 8, 9, 10, 11, 12, 13, 14, 15, 16, or 17 consecutive amino acids set forth in SEQ ID NO: 6, and a VH CDR3 region comprising an amino acid sequence that is identical to at least 7, 8, 9, 10, 11, 12, 13, 14, 15, or 16 consecutive amino acids set forth in SEQ ID NO: 7; (3) the second variable domain comprises a VL CDR1 region comprising an amino acid sequence that is identical to at least 7, 8, 9, 10, 11, 12, 13, 14, 15, or 16 consecutive amino acids set forth in SEQ ID NO: 8, a VL CDR2 region comprising an amino acid sequence that is identical to at least 3, 4, 5, 6, or 7 consecutive amino acids set forth in SEQ ID NO: 9, and a VL CDR3 region comprising an amino acid sequence that is identical to at least 3, 4, 5, 6, 7, 8, 9, or 10 consecutive amino acids set forth in SEQ ID NO: 10; and (4) the first variable domain and the second variable domain are paired in the antigen-binding region of the protein such that the antigen-binding region specifically binds human Sp17.

In some embodiments, the first variable domain comprises an amino acid sequence that has at least 90 percent sequence homology with SEQ ID NO: 3. In some specific embodiments, the first variable domain comprises an amino acid sequence that has at least 95 percent sequence homology with SEQ ID NO: 3. In some even more specific embodiments, the first variable domain comprises an amino acid sequence that has at least 98 percent sequence homology with SEQ ID NO: 3. In some very specific embodiments, the first variable domain comprises an amino acid sequence that has at least 99 percent sequence homology with SEQ ID NO: 3.

In some embodiments, the first variable domain comprises an amino acid sequence that has at least 90 percent sequence identity with SEQ ID NO: 3. In some specific embodiments, the first variable domain comprises an amino acid sequence that has at least 95 percent sequence identity with SEQ ID NO: 3. In some even more specific embodiments, the first variable domain comprises an amino acid sequence that has at least 99 percent sequence identity with SEQ ID NO: 3. In some very specific embodiments, the first variable domain comprises an amino acid sequence that is identical to SEQ ID NO: 3.

In some embodiments, the second variable domain comprises an amino acid sequence that has at least 90 percent sequence homology with SEQ ID NO: 4. In some specific embodiments, the second variable domain comprises an amino acid sequence that has at least 95 percent sequence homology with SEQ ID NO: 4. In some even more specific embodiments, the second variable domain comprises an amino acid sequence that has at least 98 percent sequence homology with SEQ ID NO: 4. In some very specific embodiments, the second variable domain comprises an amino acid sequence that has at least 99 percent sequence homology with SEQ ID NO: 4.

In some embodiments, the second variable domain comprises an amino acid sequence that has at least 90 percent sequence identity with SEQ ID NO: 4. In some specific embodiments, the second variable domain comprises an amino acid sequence that has at least 95 percent sequence identity with SEQ ID NO: 4. In some even more specific embodiments, the second variable domain comprises an amino acid sequence that has at least 99 percent sequence identity with SEQ ID NO: 4. In some very specific embodiments, the second variable domain comprises an amino acid sequence that is identical to SEQ ID NO: 4.

In some embodiments, the first variable domain comprises an amino acid sequence that has at least 90 percent sequence homology with SEQ ID NO: 3, and the second variable domain comprises an amino acid sequence that has at least 90 percent sequence homology with SEQ ID NO: 4. In some specific embodiments, the first variable domain comprises an amino acid sequence that has at least 95 percent sequence homology with SEQ ID NO: 3, and the second variable domain comprises an amino acid sequence that has at least 95 percent sequence homology with SEQ ID NO: 4. In some even more specific embodiments, the first variable domain comprises an amino acid sequence that has at least 98 percent sequence homology with SEQ ID NO: 3, and the second variable domain comprises an amino acid sequence that has at least 99 percent sequence homology with SEQ ID NO: 4. In some very specific embodiments, the first variable domain comprises an amino acid sequence that has at least 99 percent sequence homology with SEQ ID NO: 3, and the second variable domain comprises an amino acid sequence that has at least 99 percent sequence homology with SEQ ID NO: 4.

In some embodiments, the first variable domain comprises an amino acid sequence that has at least 90 percent sequence identity with SEQ ID NO: 3, and the second variable domain comprises an amino acid sequence that has at least 90 percent sequence identity with SEQ ID NO: 4. In some specific embodiments, the first variable domain comprises an amino acid sequence that has at least 95 percent sequence identity with SEQ ID NO: 3, and the second variable domain comprises an amino acid sequence that has at least 95 percent sequence identity with SEQ ID NO: 4. In some even more specific embodiments, the first variable domain comprises an amino acid sequence that has at least 99 percent sequence identity with SEQ ID NO: 3, and the second variable domain comprises an amino acid sequence that has at least 99 percent sequence identity with SEQ ID NO: 4. In some very specific embodiments, the first variable domain comprises an amino acid sequence that is identical to SEQ ID NO: 3, and the second variable domain comprises an amino acid sequence that is identical to SEQ ID NO: 4.

Various aspects of this disclosure relate to a recombinant nucleic acid, comprising a nucleotide sequence that encodes a protein that comprises an antigen-binding region, wherein (1) the antigen-binding region comprises a first variable domain and a second variable domain; (2) the first variable domain comprises an amino acid sequence that has at least 90 percent sequence homology with SEQ ID NO: 3 (such as at least 95, 97, 98, or 99 percent sequence homology); (3) the second variable domain comprises an amino acid sequence that has at least 90 percent sequence homology with SEQ ID NO: 4 (such as at least 95, 97, 98, or 99 percent sequence homology); and (4) the antibody or antigen-binding fragment thereof binds human Sp17.

In some embodiments, the first variable domain comprises an amino acid sequence that has at least 90 percent sequence identity with SEQ ID NO: 3 (such as at least 95, 97, 98, or 99 percent sequence identity), and the second variable domain comprises an amino acid sequence that has at least 90 percent sequence identity with SEQ ID NO: 4 (such as at least 95, 97, 98, or 99 percent sequence identity).

In some embodiments, the protein is a recombinant anti-Sp17 antibody as described anywhere in this disclosure.

In some embodiments, the protein is an antigen-binding fragment of a recombinant anti-Sp17 antibody as described anywhere in this disclosure.

In some embodiments, the protein is an IgG-like bispecific antibody or portion thereof as described anywhere in this disclosure. In some specific embodiments, the protein is a trifunctional antibody or portion thereof as described anywhere in this disclosure. IgG-like bispecific antibodies such as trifunctional antibodies may be encoded, for example, by two different nucleic acids such as a first nucleic acid that encodes a first heavy and light chain that binds a first epitope (such as Sp17) and a second nucleic acid that encodes a second heavy and light chain that binds a second epitope (such as a CD3) for expression of the first heavy and light chain in a first cell line and expression of the second heavy and light chain in a second cell line to avoid the pairing of heavy and light chains that bind different epitopes.

In some embodiments, the protein is a bi-specific T-cell engager (BiTE). A BiTE is a fusion protein comprising a scFV that binds an antigen (for example, Sp17) and a domain that binds a cell-surface protein expressed by a T-cell such as CD3. Examples of BiTEs include blinatumomab (also known as BLINCYTO®) and tebentafusp (also known as KIMMTRAK®). Those of ordinary skill are capable of designing BiTEs that bind Sp17 and CD3, for example, by replacing the variable regions that bind CD19 in blinatumomab or glycoprotein 100 in tebentafusp with the variable regions set forth in SEQ ID NOs: 3 & 4 (see, for example, U.S. Pat. No. 10,517,960 & 11,597,766, which are incorporated by reference in their entirety).

In some embodiments, the protein is a chimeric antigen receptor (CAR). A CAR is a fusion protein comprising (1) an N-terminal, extracellular scFV that binds an antigen (for example, Sp17), (2) a transmembrane alpha-helix, and (3) a C-terminal, intracellular signaling domain such as CD3-zeta and/or one or more intracellular signaling domains selected from CD27, CD28, CD134, and CD137. The intracellular signaling domain typically comprises an immunoreceptor tyrosine-based activation motif (ITAM). Examples of CARs include tisagenlecleucel (also known as KYMRIAH®) and axicabtagene ciloleucel (also known as YESCARTA®). Those of ordinary skill are capable of designing CARs that bind Sp17, for example, by replacing the variable regions that bind CD19 in tisagenlecleucel or axicabtagene ciloleucel with the variable regions set forth in SEQ ID NOs: 3 & 4 (see, for example, U.S. Pat. Nos. 7,446,190, 7,741,465 & 9,499,629, which are incorporated by reference in their entirety).

In some embodiments, the recombinant nucleic acid comprises a nucleotide sequence that is at least 70 percent identical to SEQ ID NO: 1. In some specific embodiments, the recombinant nucleic acid comprises a nucleotide sequence that is at least 80 percent identical to SEQ ID NO: 1. In some even more specific embodiments, the recombinant nucleic acid comprises a nucleotide sequence that is at least 90 percent identical to SEQ ID NO: 1. In some very specific embodiments, the recombinant nucleic acid comprises a nucleotide sequence that is at least 95 percent identical to SEQ ID NO: 1.

In some embodiments, the recombinant nucleic acid comprises a nucleotide sequence that encodes an amino acid sequence that has at least 90 percent sequence homology with SEQ ID NO: 11. In some specific embodiments, the recombinant nucleic acid comprises a nucleotide sequence that encodes an amino acid sequence that has at least 95 percent sequence homology with SEQ ID NO: 11. In some even more specific embodiments, the recombinant nucleic acid comprises a nucleotide sequence that encodes an amino acid sequence that has at least 98 percent sequence homology with SEQ ID NO: 11. In some very specific embodiments, the recombinant nucleic acid comprises a nucleotide sequence that encodes an amino acid sequence that has at least 99 percent sequence homology with SEQ ID NO: 11.

In some embodiments, the recombinant nucleic acid comprises a nucleotide sequence that encodes an amino acid sequence that is at least 90 percent identical to SEQ ID NO: 11. In some specific embodiments, the recombinant nucleic acid comprises a nucleotide sequence that encodes an amino acid sequence that is at least 95 percent identical to SEQ ID NO: 11. In some even more specific embodiments, the recombinant nucleic acid comprises a nucleotide sequence that encodes an amino acid sequence that is at least 98 percent identical to SEQ ID NO: 11. In some very specific embodiments, the recombinant nucleic acid comprises a nucleotide sequence that encodes an amino acid sequence that is at least 99 percent identical to SEQ ID NO: 11.

In some embodiments, the recombinant nucleic acid comprises a nucleotide sequence that is at least 70 percent identical to SEQ ID NO: 2. In some specific embodiments, the recombinant nucleic acid comprises a nucleotide sequence that is at least 80 percent identical to SEQ ID NO: 2. In some even more specific embodiments, the recombinant nucleic acid comprises a nucleotide sequence that is at least 90 percent identical to SEQ ID NO: 2. In some very specific embodiments, the recombinant nucleic acid comprises a nucleotide sequence that is at least 95 percent identical to SEQ ID NO: 2.

In some embodiments, the recombinant nucleic acid comprises a nucleotide sequence that encodes an amino acid sequence that has at least 90 percent sequence homology with SEQ ID NO: 12. In some specific embodiments, the recombinant nucleic acid comprises a nucleotide sequence that encodes an amino acid sequence that has at least 95 percent sequence homology with SEQ ID NO: 12. In some even more specific embodiments, the recombinant nucleic acid comprises a nucleotide sequence that encodes an amino acid sequence that has at least 98 percent sequence homology with SEQ ID NO: 12. In some very specific embodiments, the recombinant nucleic acid comprises a nucleotide sequence that encodes an amino acid sequence that has at least 99 percent sequence homology with SEQ ID NO: 12.

In some embodiments, the recombinant nucleic acid comprises a nucleotide sequence that encodes an amino acid sequence that is at least 90 percent identical to SEQ ID NO: 12. In some specific embodiments, the recombinant nucleic acid comprises a nucleotide sequence that encodes an amino acid sequence that is at least 95 percent identical to SEQ ID NO: 12. In some even more specific embodiments, the recombinant nucleic acid comprises a nucleotide sequence that encodes an amino acid sequence that is at least 98 percent identical to SEQ ID NO: 12. In some very specific embodiments, the recombinant nucleic acid comprises a nucleotide sequence that encodes an amino acid sequence that is at least 99 percent identical to SEQ ID NO: 12.

In some embodiments, the recombinant nucleic acid comprises an origin of replication, wherein the recombinant nucleic acid is a plasmid.

Various aspects of this disclosure relate to a viral vector, comprising the recombinant nucleic acid as described anywhere in this disclosure. In some embodiments, the vector has a tropism for human leukocytes. In some specific embodiments, the vector has a tropism for human T-cells, natural killer cells, or monocytes. In some very specific embodiments, the viral vector is an adenovirus vector, an adeno-associated virus vector, a lentiviral vector, or a gamma-retroviral vector. Viral vectors may be used, for example, to introduce a recombinant nucleic acid encoding a CAR into a leukocyte to produce a transgenic leukocyte that expresses the CAR for use as a cancer immunotherapy.

Various aspects of this disclosure relate to a cell, comprising a recombinant nucleic acid as described anywhere in this disclosure or a viral vector as described anywhere in this disclosure.

In some embodiments, the cell is a prokaryote such as *E. coli*, and the cell is used for cloning or propagating the recombinant nucleic acid. When the cell is a prokaryote, then the recombinant nucleic acid generally includes an origin of replication for propagation as well as an antibiotic resistance gene to provide a selective advantage for cells that comprise the recombinant nucleic acid.

In some embodiments, the cell is a bacterial cell.

In some embodiments, the cell is mammalian cell. In some specific embodiments, the cell is an immortalized mammalian cell line. In some very specific embodiments, the cell is a CHO cell (Chinese hamster ovary), a HEK cell (human embryonic kidney), such as a HEK293 cell, a NS0 cell (murine myeloma cell), a Sp2/0 cell (murine myeloma cell), or a PER.C6® cell (human retina cell). Immortalized mammalian cell lines are generally used to express proteins for use as therapeutics such as therapeutic antibodies (including, for example, the human anti-Sp17 antibody described herein). Mammalian cells generally ensure the fidelity of the tertiary and quaternary structure of the variable regions and other regions of an Sp17-binding protein as well as the fidelity of post-translational modifications such as glycosylation patterns. Mammalian cells may also be used, for example, to manufacture viral vectors as described herein. The recombinant nucleic acid may be present in the cell either transiently or stably.

In some embodiments, the cell is a mammalian cell, and the mammalian cell expresses the protein.

In some embodiments, the cell is a mammalian cell, the mammalian cell expresses a viral vector, and the recombinant nucleic acid comprises a packaging signal for packaging the recombinant nucleic acid in the viral vector.

In some embodiments, the cell is a tissue culture cell. In some specific embodiments, the cell is a tissue culture cell, and the tissue culture cell expresses the protein. In some specific embodiments, the cell is a tissue culture cell; the tissue culture cell expresses a viral vector; and the recombinant nucleic acid comprises a packaging signal for packaging the recombinant nucleic acid in the viral vector.

In some embodiments, the cell is a peripheral blood mononuclear cell (PBMC). In some specific embodiments the cell is a human PBMC. In some specific embodiments, the cell is a T-cell, a natural killer cell, a monocyte, a macrophage, or a dendritic cell. In some very specific embodiments, the cell is a human T-cell, a human natural killer cell, a human monocyte, a human macrophage, or a human dendritic cell. PBMCs may be transfected with a recombinant nucleic acid to express a CAR such that the PBMCs may be used as a cancer immunotherapy, for example, such as a CAR-T cell, a CAR-NK cell, CAR-monocyte, CAR-macrophage, or CAR-DC.

In some embodiments, the cell is a leukocyte, and the nucleotide sequence encodes a protein that is a CAR. In some specific embodiments, the cell is a human leukocyte, and the nucleotide sequence encodes a protein that is a CAR. In some very specific embodiments, the cell is a human leukocyte, the nucleotide sequence encodes a protein that is a CAR, and the human leukocyte expresses the CAR.

In some embodiments, the cell is a PBMC, and the nucleotide sequence encodes a protein that is a CAR. In some specific embodiments, the cell is a human PBMC, and the nucleotide sequence encodes a protein that is a CAR. In some very specific embodiments, the cell is a human PBMC, the nucleotide sequence encodes a protein that is a CAR, and the human PBMC expresses the CAR.

In some embodiments, the cell is a T-cell, a natural killer cell, a monocyte, a macrophage, or a dendritic cell, and the nucleotide sequence encodes a protein that is a CAR. In some specific embodiments, the cell is a human T-cell, a human natural killer cell, a human monocyte, a human macrophage, or a human dendritic cell, and the nucleotide sequence encodes a protein that is a CAR. In some very specific embodiments, the cell is a human T-cell, a human natural killer cell, a human monocyte, a human macrophage, or a human dendritic cell, the nucleotide sequence encodes a protein that is a CAR, and the cell expresses the CAR.

Various aspects of this disclosure relate to a Fab fragment that binds Sp17 and that comprises CDRs that have sequence homology with the amino acid sequences set forth in SEQ ID NO: 3-6. A Fab may comprise amino acid sequences that have, for example, at least 90, 95, 97, 98, or 99 percent sequence homology with the sequences set forth in SEQ ID NO: 3-6 or at least 90, 95, 97, 98, or 99 percent sequence identity with the sequences set forth in SEQ ID NO: 3-6. In some embodiments, the Fab fragment is encoded by a recombinant nucleic acid as described anywhere in this disclosure.

Various aspects of this disclosure relate to an antibody comprising a Fab fragment described anywhere in this disclosure. In some embodiments, the antibody is encoded by a recombinant nucleic acid as described anywhere in this disclosure.

Various aspects of this disclosure relate to a bi-specific antibody that comprises CDRs that have sequence homology with the amino acid sequences set forth in SEQ ID NO: 3-6. A bi-specific antibody may comprise amino acid sequences that have, for example, at least 90, 95, 97, 98, or 99 percent sequence homology with the sequences set forth in SEQ ID NO: 3-6 or at least 90, 95, 97, 98, or 99 percent sequence identity with the sequences set forth in SEQ ID NO: 3-6. In some embodiments, the bi-specific antibody is encoded by a recombinant nucleic acid as described anywhere in this disclosure.

Various aspects of this disclosure relate to a BiTE that comprises CDRs that have sequence homology with the amino acid sequences set forth in SEQ ID NO: 3-6. A BiTE may comprise amino acid sequences that have, for example, at least 90, 95, 97, 98, or 99 percent sequence homology with the sequences set forth in SEQ ID NO: 3-6 or at least 90, 95, 97, 98, or 99 percent sequence identity with the sequences set forth in SEQ ID NO: 3-6. In some embodiments, the BiTE is encoded by a recombinant nucleic acid as described anywhere in this disclosure.

Having described various features of this disclosure both generally and specifically in the preceding detailed description, the following exemplification provides a specific example of the preparation of the subject matter described herein. By way of this example, and in the context of the preceding detailed description, the skilled person will immediately recognize variations to the method set forth in the example (such as by engineering a BiTE, scFv, or chimeric antigen receptor instead of an IgG). The following exemplification is illustrative only and shall not limit this disclosure or any patent claim that matures from this disclosure. Any patent claim that matures from this disclosure shall instead be limited by the explicit features recited in the claim in the context of its claim dependency and according to conventional principles of claim construction as applied in view of this disclosure.

EXEMPLIFICATION

Example 1. Identification of Human Variable Regions for an Anti-Sp17 Antibody Based on Human Diversity A Fab phage display library was constructed from peripheral blood obtained from 120 healthy human donors. Briefly, this library was constructed by randomly combining nucleotide sequences encoding immunoglobulin heavy chain variable regions with nucleotide sequences encoding immunoglobulin light chain variable regions. The library had a diversity of approximately 1 trillion combinations. Biopanning of the library identified twelve positive colonies, and nucleotide sequencing of the colonies identified two distinct clones. A single clone was identified as binding Sp17 by ELISA. The nucleotide sequences of the human VH and VL regions of the antibody are set forth in Table 1 below. The variable regions have the amino acid sequences set forth in Table 2 below and the CDRs set forth in Table 3 below.

TABLE 1

Nucleotide sequences of anti-Sp17 VH and VL regions identified
by bio-panning a Fab phage-display library of ~1 trillion human
Fabs developed from peripheral blood samples of 120 human subjects

```
SEQ ID       Sequence 10       20        30        40
NO.   Region 12345678901234567890123456789012345678901234567890

1     VH   CAGGTACAGCTGCAGCAGTCAGGGGCTGAGGTGAAGAAGCCTGGGTCCTC
             GGTGAAGGTCTCCTGCAAGGCTTCTGGAGGCACCTTCAGCAGCTATGCTA
             TCAGCTGGGTGCGACAGGCCCCTGGACAAGGGCTTGAGTGGATGGGAAGG
             ATCATCCCTATCCTTGGTATAGCAAACTACGCACAGAAGTTCCAGGGCAG
             AGTCACGATTACCGCGGACAAATCCACGAGCACAGCCTACATGGAGCTGA
             GCAGCCTGAGATCTGAGGACACGGCCGTGTATTACTGTGCGAGACCCTCC
             GAAGAGGTGGTAGCTGCTTACGGTGCTTTTGATATCTGGGGCCAAGGGAC
             CACGGTCACCGTCTCAAGC

2     VL   GAAATTGTGCTGACTCAGTCTCCACTCTCCCTGCCCGTCAGACCTGGGGA
             GCCGGCCTCCATCTCCTGCAGGGCTAGTCAGAGCCTCCTGCGTAGTGACG
             GATTCAACTACTTGGATTGGTACCTGCAGAAGCCAGGGCAGTCTCCACAG
             CTCCTGGTCTATTTGGGTTCTAATCGGGCCTCCGGGGTCCCTGACAGGTT
             CAGTGGCAGTGGATCAGGCACAGATTTTACACTGAAAATCAGCAGAGTGG
             AGGCTGAGGATGTTGGGGTTTATTACTGCATGCAAGCTGTACAAACTCCG
             TACATTTTTGGCCAGGGGACCAAGCTGGAGATCAAA
```

TABLE 2

Amino acid sequences of anti-Sp17 VH and VL regions identified by
bio-panning a Fab phage-display library of ~1 trillion human Fabs
developed from peripheral blood samples of 120 human subjects

```
SEQ
ID            Sequence 10        20        30        40
NO. Region   12345678901234567890123456789012345678901234567890

3     VH   QVQLQQSGAEVKKPGSSVKVSCKASGGTFSSYAISWVRQAPGOGLEWMGR
             IIPILGIANYAQKFQGRVTITADKSTSTAYMELSSLRSEDTAVYYCARPS
             EEVVAAYGAFDIWGQGTTVTVSS

4     VL   EIVLTQSPLSLPVRPGEPASISCRASQSLLRSDGFNYLDWYLQKPGOSPQ
             LLVYLGSNRASGVPDRFSGSGSGTDFTLKISRVEAEDVGVYYCMQAVQTP
             YIFGQGTKLEIK
```

TABLE 3

Amino acid sequences of CDRs of the
VH and VL regions identified by bio-
panning a Fab phage-display library
of ~1 trillion human Fabs developed
from peripheral blood samples of
120 human subjects

| SEQ ID NO. | Region | Sequence 10 12345678901234567 |
|---|---|---|
| 5 | VH CDR1 | GGTFSSYAIS |
| 6 | VH CDR2 | RIIPILGIANYAQKFQG |
| 7 | VH CDR3 | ARPSEEVVAAYGAFDI |
| 8 | VL CDR1 | RASQSLLRSDGFNYLD |
| 9 | VL CDR2 | LGSNRAS |
| 10 | VL CDR3 | MQAVQTPYIF |

Figure 2:
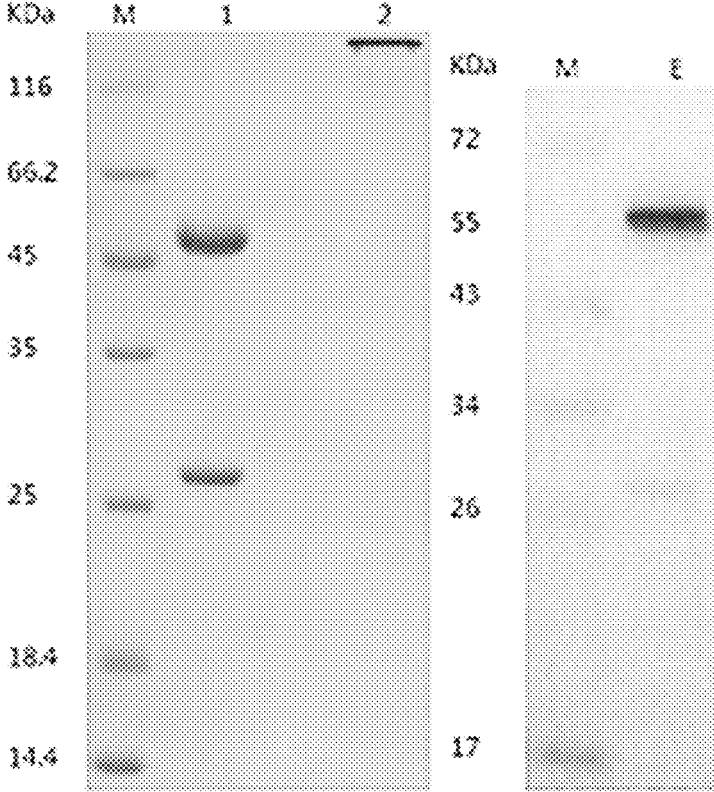
FIG. 2 consists of two panels. The left panel is a Coomassie-blue stained SDS-PAGE gel loaded with a molecular weight standard (lane M), the anti-Sp17 antibody chAB2 under reducing conditions (lane 1), and the anti-Sp17 antibody chAB2 under non-reducing conditions (lane 2). The right panel is a western blot of an SDS-PAGE gel loaded with a molecular weight standard (lane M) and the anti-Sp17 antibody chAB2 under reducing conditions (lane E), in which chAB2 was detected using enhanced chemiluminescence (ECL) with anti-mouse secondary antibodies.
Figure 3:
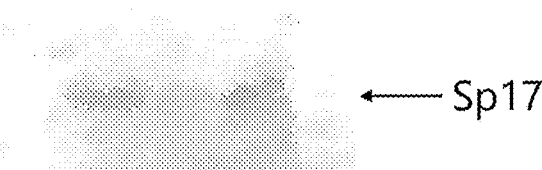
FIG. 3 is a western blot of an SDS-PAGE gel loaded with a molecular weight standard (lane M) and with Sp17 protein (lanes 1, 2, & 3), in which the Sp17 protein was detected with the anti-Sp17 antibody chAB2.
Figure 4:
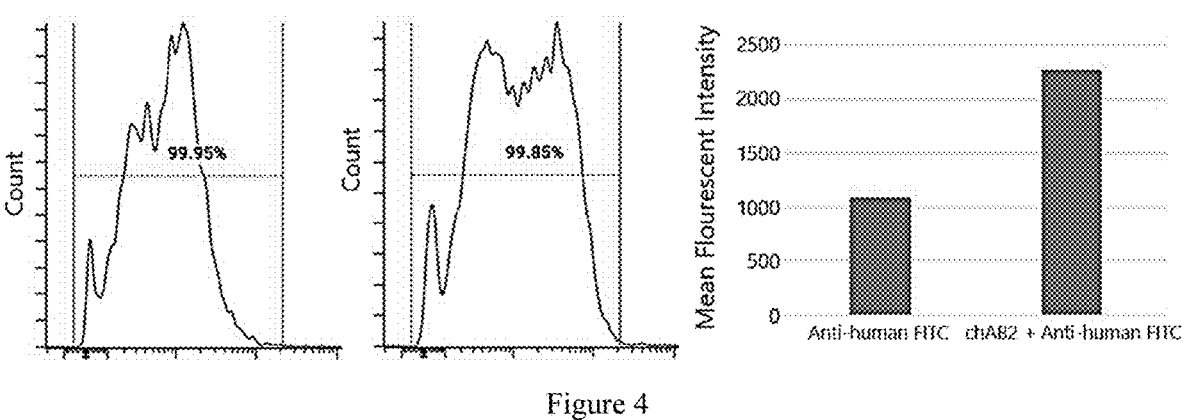
FIG. 4 consists of three panels. The left panel is a graph that depicts flow cytometry results for ID8 cells incubated with an anti-mouse fluorescein isothiocyanate (FITC) antibody, but without a primary antibody. The middle panel is a graph that depicts flow cytometry results for ID8 cells labeled with the anti-Sp17 antibody chAB2 and the anti-mouse FITC antibody. The right panel is a histogram that displays an increased mean fluorescent intensity for the ID8 cells labeled with chAB2 and the anti-mouse FITC antibody of the middle panel relative to ID8 cells incubated with the anti-mouse FITC antibody alone of the left panel.
Figure 5:
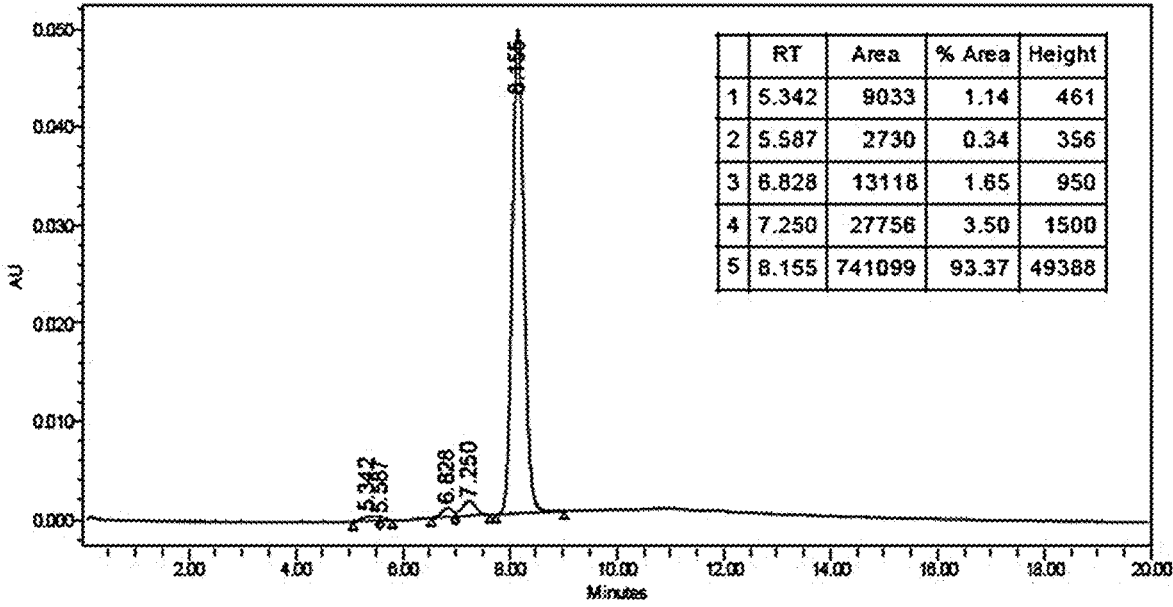
FIG. 5 is a high-performance liquid chromatography (HPLC) chromatogram that demonstrates that anti-Sp17 antibody chAB2 preparations can be manufactured at 93 percent purity.
Figure 6:
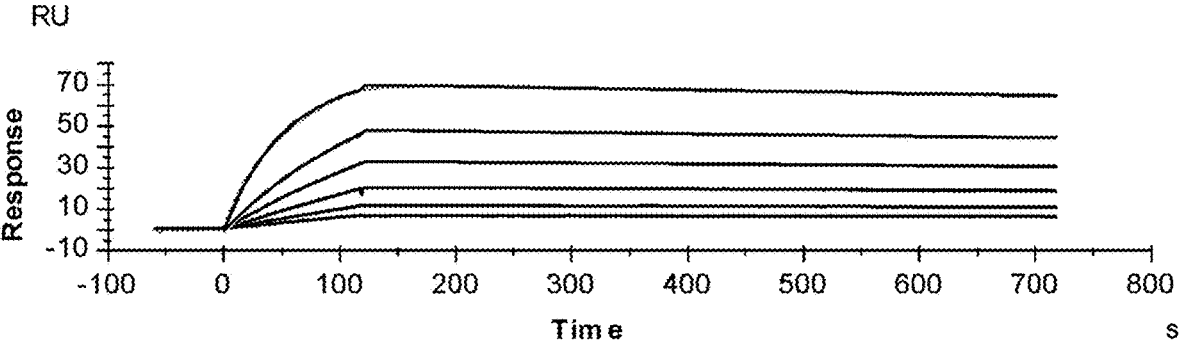
FIG. 6 is a graph that displays surface plasmon resonance data for the anti-Sp17 antibody chAB2 binding to a recombinant 6His-Sp17 protein. The lines correspond, from highest to lowest, to fitted cycles for 300 nanomolar, 100 nanomolar, 50 nanomolar, 25 nanomolar, 12.5 nanomolar, and 6.25 nanomolar concentrations of 6His-Sp17. This data was used to calculate an association rate constant (ka) for chAB2 to Sp17 of 62,600 per mole per second, a dissociation rate constant (kd) of 0.000 129 8 per second, and a dissociation constant (KD) of 2.073 nanomolar.

Example 2. Engineering a Mouse-Human Chimeric Anti-Sp17 IgG2a/KAPPA Monoclonal Antibody The nucleotide sequences encoding the VH and VL regions of Example 1 were cloned into a mouse IgG2a heavy chain gene and a mouse kappa light chain gene, respectively, and expressed in CHO-S cells to produce a mouse-human chimeric antibody, which was named chAB2. Successful generation of the antibody was confirmed by SDS-PAGE and western blotting using anti-mouse heavy and light chain antibodies and recombinant Sp17 protein (FIGS. 2 & 3). The chAB2 antibody was reactive to mouse surface Sp17 protein expressed on the mouse ovarian cancer cell line ID8 (FIG. 4). HPLC of the chAB2 antibody preparation showed 93 precent purity (FIG. 5). Surface plasmon resonance with a Biacore™ T200 was used to determine a KD for chAB2 and Sp17 of 2.073 nanomolar (FIG. 6).

The specificity of the chAB2 antibody for Sp17 was determined with immunohistochemistry on a normal tissue microarray, which consisted of 33 normal tissues obtained from 2-3 human donors per tissue. The normal tissues included brain, eye, adrenal gland, hypophyseal, thyroid, parathyroid, tonsil, thymus, spleen, heart, lung, larynx, esophagus, stomach, small intestine, colon, liver, pancreas, salivary gland, kidney, bone, skeletal, skin, peripheral nerve, mesothelial, breast, ovary, endometrium, cervix, testis, and prostate. The chAB2 antibody bound to testis and did not bind to normal tissues.

Example 3. Engineering a Human Anti-Sp17 IgG4/KAPPA Monoclonal Antibody

Figure 7:
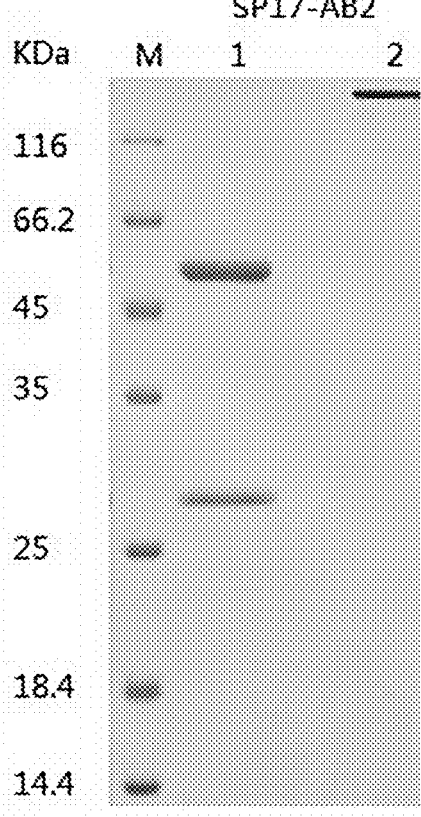
FIG. 7 is an image of an SDS-PAGE gel loaded with a molecular weight standard (lane M) and the anti-Sp17 antibody SP17-AB2 under reducing conditions (lane 1) and non-reducing conditions (lane 2).
Figure 8:
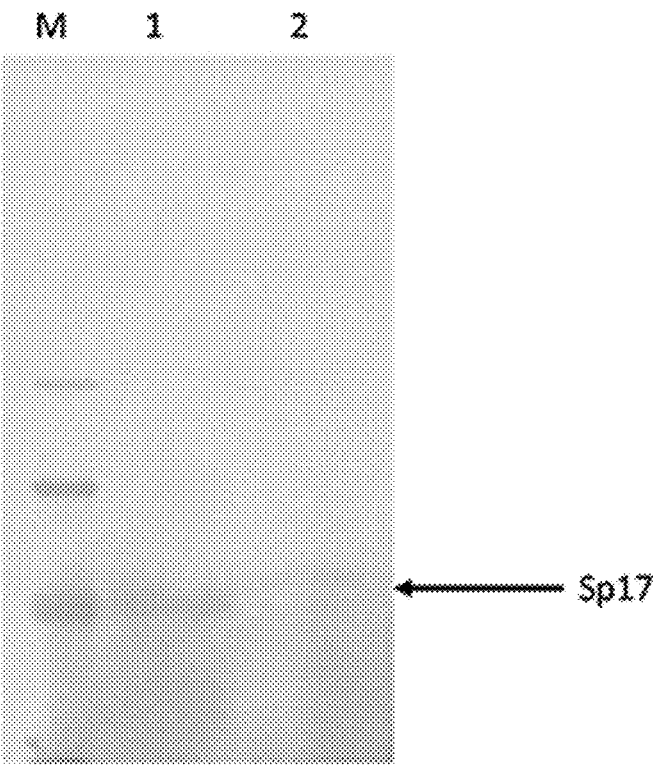
FIG. 8 is a western blot of an SDS-PAGE gel loaded with a molecular weight standard (lane M), with Sp17 protein (lane 1), and with a tumor cell lysate (lane 2), in which the Sp17 protein was detected with the anti-Sp17 antibody SP17-AB2.

The VH and VL nucleotide sequences of Example 1 were cloned into a human IgG4 heavy chain gene and a human kappa light chain gene, respectively. A Ser228Pro mutation was introduced in the heavy chain to reduce non-specific Fc receptor gamma binding. The resultant antibody was named SP17-AB2. Successful cloning was confirmed by sequence analysis. The amino acid sequences of the heavy chain and light chain are shown in Table 4, and the Ser228Pro mutation is underlined in SEQ ID NO: 11. Successful expression of the SP17-AB2 antibody was confirmed by SDS-PAGE (FIG. 7), and the ability of the SP17-AB2 antibody to bind Sp17 protein was confirmed by western blot (FIG. 8).

production of the immunoconjugate was confirmed by reducing the immunoconjugate with excess dithiothreitol followed by mass spectroscopy analysis to determine that SP17-AB2-DXD comprises a deruxtecan to SP17-AB2 ratio of about 7.93 indicating that, on average, an individual SP17-AB2-DXD molecule comprises about eight deruxtecan moieties. This drug-to-antibody ratio is notably significantly greater than most FDA-approved antibodies.

SK-OV-3 cells were seeded at 1000, 2000, or 3000 cells per well and incubated overnight in advance of a cytotox-

TABLE 4

Amino Acid Sequences of the human anti-Sp17 antibody SP17-AB2

```
SEQ
ID           Sequence 10        20        30        40
NO.  Region  12345678901234567890123456789012345678901234567890

11   Full    MDMRVPAQLLGLLLLWLRGARCQVQLQQSGAEVKKPGSSVKVSCKASGGT
     Heavy   FSSYAISWVRQAPGQGLEWMGRIIPILGIANYAQKFQGRVTITADKSTST
     Chain   AYMELSSLRSEDTAVYYCARPSEEVVAAYGAFDIWGQGTTVTVSSASTKG
             PSVFPLAPCSRSTSESTAALGCLVKDYFPEPVTVSWNSGALTSGVHTFPA
             VLQSSGLYSLSSVVTVPSSSLGTKTYTCNVDHKPSNTKVDKRVESKYGPP
             CPPCPAPEFLGGPSVFLFPPKPKDTLMISRTPEVTCVVVDVSQEDPEVQF
             NWYVDGVEVHNAKTKPREEQFNSTYRVVSVLTVLHQDWLNGKEYKCKVSN
             KGLPSSIEKTISKAKGQPREPQVYTLPPSQEEMTKNQVSLTCLVKGFYPS
             DIAVEWESNGQPENNYKTTPPVLDSDGSFFLYSRLTVDKSRWQEGNVFSC
             SVMHEALHNHYTQKSLSLSLGK 12   Full    MDMRVPAQLLGLLLLWLRGARCEIVLTQSPLSLPVRPGEPASISCRASQS
     Light   LLRSDGFNYLDWYLQKPGQSPQLLVYLGSNRASGVPDRFSGSGSGTDFTL
     Chain   KISRVEAEDVGVYYCMQAVQTPYIFGQGTKLEIKRTVAAPSVFIFPPSDE
             QLKSGTASVVCLLNNFYPREAKVQWKVDNALQSGNSQESVTEQDSKDSTY
             SLSSTLTLSKADYEKHKVYACEVTHQGLSSPVTKSFNRGEC 13   Signal  MDMRVPAQLLGLLLLWLRGARC
     Peptide
```

Based on the foregoing, the SP17-AB2 antibody may be particularly useful as a therapeutic antibody to treat cancers that express Sp17.

Example 4. Engineering Anti-Sp17 Immunoconjugates with Deruxtecan

Figure 9A:
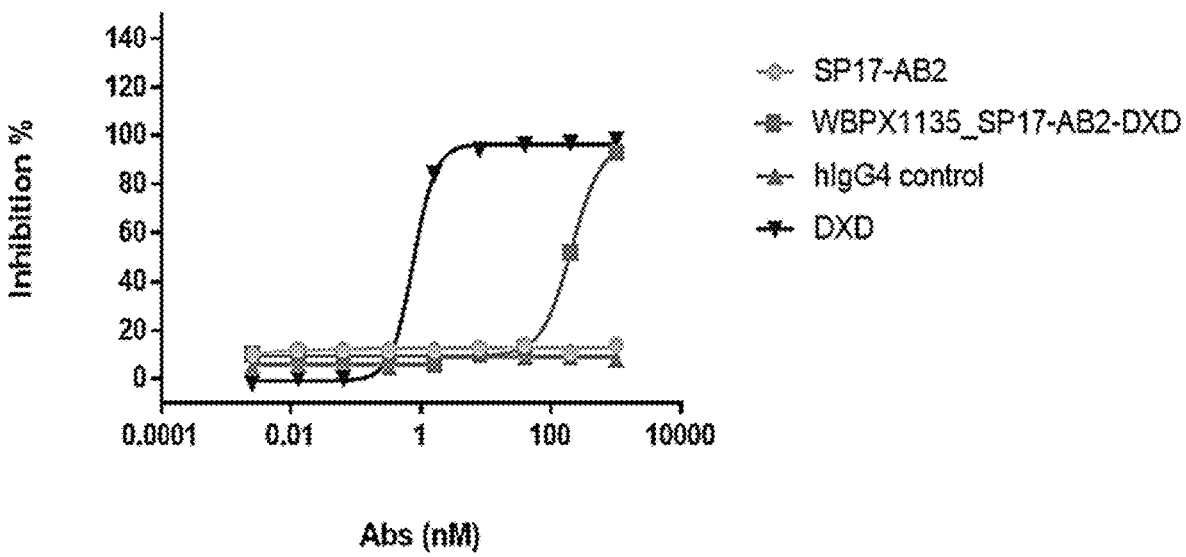
FIGS. 9A, 9B, and 9C are graphs that depict immunotherapeutic concentration (x-axis, nanomolar) versus cytotoxicity against SK-OV-3 cells (y-axis, percent cytotoxicity) for immunotherapeutics selected from the monomeric antibody SP17-AB2 (circles, •), the monomeric immunoconjugate SP17-AB2-DXD (squares, ■), a control human IgG4 antibody (upright triangles, ▲), and deruxtecan (inverted triangles, ▼).
Figure 9B:
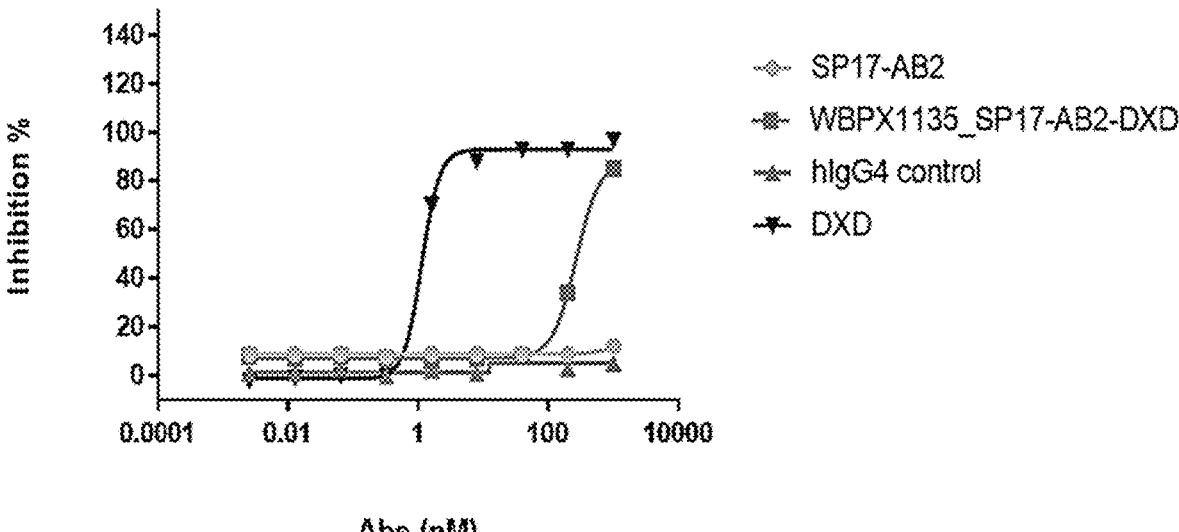
Figure 9C:
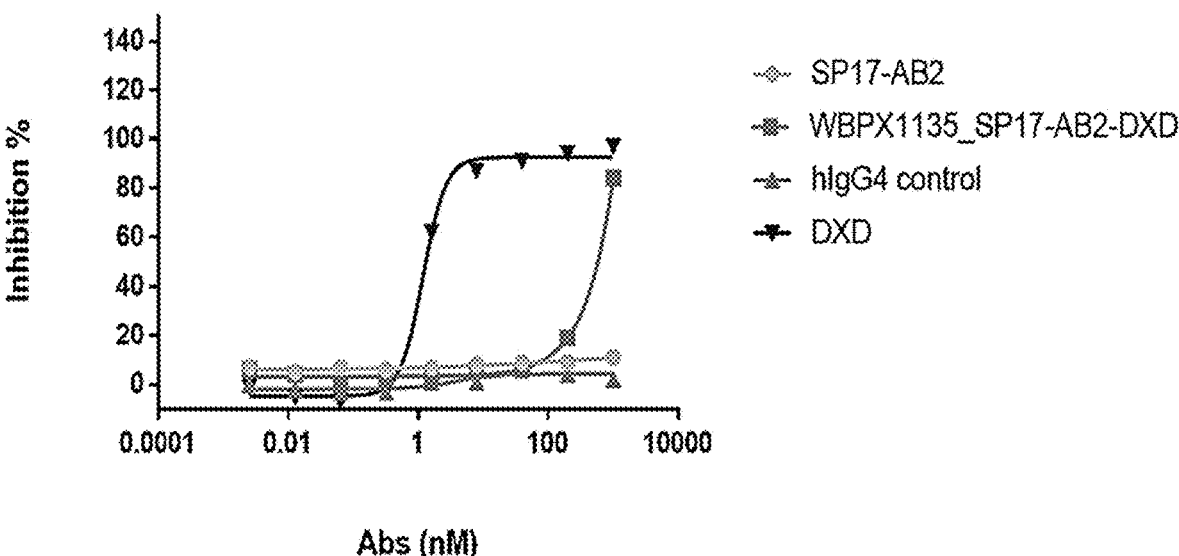

The SP17-AB2 antibody as described in Example 3 was crosslinked to deruxtecan using the conjugation strategy set forth in U.S. Pat. No. 10,729,782, which is incorporated by reference in its entirety, to produce an immunoconjugate SP17-AB2-DXD. The deruxtecan pharmaceutical agent displays antineoplastic cytotoxicity based on its exatecan moiety, which is a topoisomerase inhibitor, and which is covalently crosslinked to SP17-AB2 by a linker and a disulfide bond as described in U.S. Pat. No. 10,729,782. Successful icity assay. SK-OV-3 cells are human ovarian cancer cells that express Sp17 and that are resistant to various chemotherapeutics including cisplatin, doxorubicin, and diphtheria toxin. The SK-OV-3 cells were treated with various concentrations of the SP17-AB2 antibody, the SP17-AB2-DXD immunoconjugate, a control human IgG4 antibody (hIgG4), or deruxtecan alone (DXD). The cells were incubated for 5 or 6 additional days, and cytotoxicity was then measured using a luminescence assay and EnVision™ plate reader (PerkinElmer, Massachusetts, United States). The SP17-AB2-DXD immunoconjugate displayed superior cytotoxicity relative to the naked SP17-AB2 antibody and the human IgG4 control (FIGS. 9A-9C; Table 5).

TABLE 5

The IC50 and Cytotoxicity of Immunoconjugate SP17-AB2-DXD are Superior to Naked Antibody SP17-AB2 Against Human Ovarian Cancer Cells

| Treatment | SK-OV-3 cells at 1000 cells/well | | SK-OV-3 cells at 2000 cells/well | | SK-OV-3 cells at 3000 cells/well | |
|---|---|---|---|---|---|---|
| | IC50 (nM) | Max Cytotoxicity | IC50 (nM) | Max Cytotoxicity | IC50 (nM) | Max Cytotoxicity |
| SP17-AB2 | | 14 | | 12 | | 11 |
| SP17-AB2-DXD | 207 | 93 | 268 | 85 | | 84 |
| hIgG4 control | | 10 | | 8 | | 8 |
| deruxtecan | 0.75 | 98 | 1.1 | 97 | 1.2 | 97 |

Figure 10:
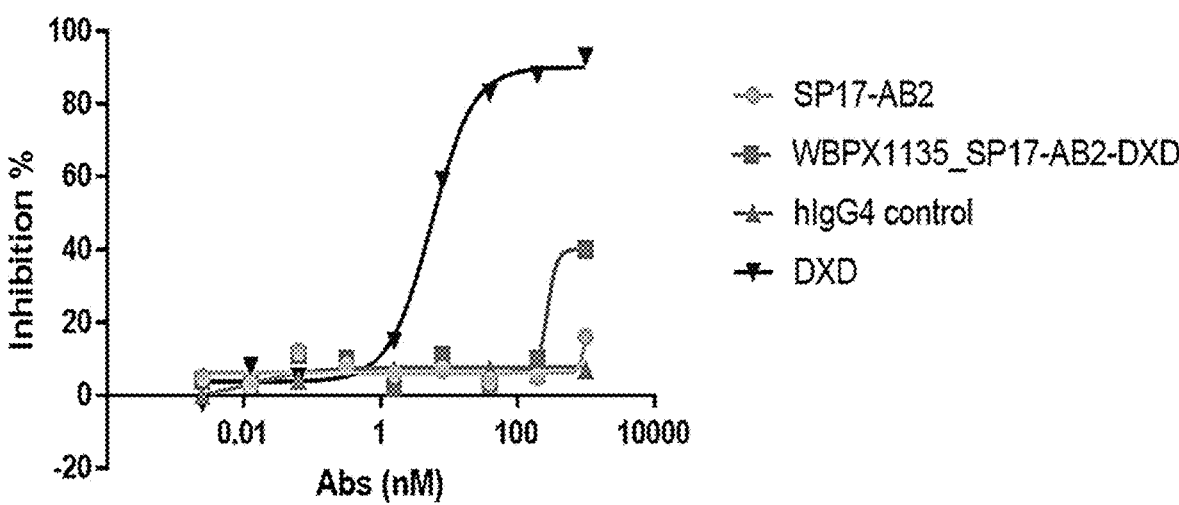
FIG. 10 is a graph that depicts immunotherapeutic concentration (x-axis, nanomolar) versus cytotoxicity against ID8 cells (y-axis, percent cytotoxicity) for immunotherapeutics selected from the monomeric antibody SP17-AB2 (circles, •), the immunoconjugate SP17-AB2-DXD (squares, ■), hIgG4 (upright triangles, ▲), and deruxtecan (inverted triangles, ▼).

ID8 cells were seeded at 250 or 300 cells per well and incubated overnight to establish a confluency of about 90 percent in advance of a second cytotoxicity assay. The cells were then treated with various concentrations of either the SP17-AB2 antibody, the SP17-AB2-DXD immunoconjugate, hIgG4, or deruxtecan alone. The cells were incubated for 3 additional days, and then cytotoxicity was measured. The SP17-AB2-DXD immunoconjugate displayed superior cytotoxicity relative to the naked SP17-AB2 antibody and the human IgG4 control (FIG. 10; Table 6).

TABLE 6

The Cytotoxicity of Immunoconjugate SP17-AB2-DXD is Superior to Naked Antibody SP17-AB2 Against Mouse Ovarian Cancer Cells

| Treatment | ID8 cells at 250 cells/well Max Cytotoxicity | ID8 cells at 500 cells/well Max Cytotoxicity |
|---|---|---|
| SP17-AB2 | 29 | 16 |
| SP17-AB2-DXD | 32 | 40 |
| hIgG4 control | 13 | 10 |
| deruxtecan | 94 | 93 |

No patent claim that matures from this disclosure shall be interpreted as requiring any feature of the foregoing Exemplification. Any methods described in the claims or specification shall not be interpreted to require the steps to be performed in a specific order unless expressly stated otherwise. The methods shall be interpreted to provide support to perform the recited steps in any order unless expressly stated otherwise.

Certain features described in the context of separate implementations can also be implemented in combination in a single implementation. Conversely, various features that are described in the context of a single implementation can also be implemented in multiple implementations separately or in any suitable sub-combination. Moreover, although features may be described above in certain combinations and even initially claimed as such, one or more features from a claimed combination can be excised from the combination, and the claimed combination may be directed to a sub-combination or variation of a sub-combination.

The example configurations described in this document do not represent all the examples that may be implemented or that fall within the scope of the claims. The term "example" shall be interpreted to mean "serving as an example, instance, or illustration," and not "preferred" or "advantageous over other examples."

Articles such as "the," "a," and "an" can connote the singular or plural. The word "or" when used without a preceding "either" (or other similar language indicating that "or" is unequivocally meant to be exclusive, for example, only one of x or y) shall be interpreted to be inclusive (for example, "x or y" means one or both of x and y).

The term "and/or" shall also be interpreted to be inclusive (for example, "x and/or y" means one or both of x and y). In situations where "and/or" or "or" are used as a conjunction for a group of three or more items, then the group shall be interpreted to include one item alone, all the items together, or any combination or number of the items.

The terms "has," "contain(s)," and "include(s)" shall be interpreted to be synonymous with the term "comprise(s)" and as inclusive or open-ended such as to not exclude additional unrecited subject matter. Use of the four preceding terms also discloses and provides support for narrower alternative implementations, in which these terms are replaced by "consisting" or "consisting essentially of," which are closed as to exclude additional unrecited subject matter.

Unless otherwise indicated, all numbers or expressions, such as those expressing concentrations, ratios, counts, and the like, used in the specification (other than the claims) are understood to be modified in all instances by the term "approximately." At the very least, and not as an attempt to limit the application of the doctrine of equivalents to the claims, each numerical parameter recited in the specification or claims that is modified by the term "approximately" should be construed in light of the number of recited significant digits and by applying ordinary rounding techniques. All disclosed ranges are to be understood to encompass and provide support for claims that recite any subranges or any and all individual values subsumed by each range. For example, a stated range of "at least 90 percent" shall be construed as including support for at least 90 percent, at least 95 percent, at least 97 percent, at least 98 percent, at least 99 percent, at least 99.5 percent, at least 99.6 percent, at least 99.7 percent, at least 99.8 percent, and at least 99.9 percent.

The terms recited in the claims should be given their ordinary and customary meaning as determined by reference to relevant entries in widely used general dictionaries, relevant technical references, commonly understood meanings by those in the art, and the like with the understanding that the broadest meaning imparted by any one or combination of these sources should be given to the claim terms (for example, two or more relevant references should be combined to provide the broadest meaning of the combination of references) subject only to the following two exceptions: (a) when a term is used in a manner that is more expansive than its ordinary and customary meaning, then the term should be given its ordinary and customary meaning plus the additional expansive meaning, and (b) when a term has been explicitly defined to have a different meaning by reciting the term and its definition along with the phrase "in this disclosure" or similar language, then the term shall be limited to the definition. References to specific examples shall not invoke the foregoing exception (b) or otherwise restrict the scope of the recited claim terms. Other than situations where the foregoing exception (b) applies, nothing contained in this document should be considered a disclaimer or disavowal of claim scope.

The subject matter recited in the claims is not coextensive with and should not be interpreted to be coextensive with any implementation, feature, or combination of features described or illustrated in this document. This is true even if only a single implementation of the feature or combination of features is illustrated and described.

What is claimed is:

1. A recombinant nucleic acid, comprising a nucleotide sequence that encodes a protein that comprises an antigen-binding region, wherein:

the antigen-binding region comprises a first variable domain and a second variable domain;

wherein the first variable domain comprises a VH CDR1 region comprising the amino acid sequence of SEQ ID NO: 5, a VH CDR2 region comprising the amino acid sequence of SEQ ID NO: 6, and a VH CDR3 region comprising the amino acid sequence of SEQ ID NO: 7; and wherein the second variable domain comprises a VL CDR1 region comprising the amino acid sequence of SEQ ID NO: 8, a VL CDR2 region comprising the amino acid sequence of SEQ ID NO: 9, and a VL CDR3 region comprising the amino acid sequence of SEQ ID NO: 10; and wherein the first variable domain and the second variable domain are paired in the antigen-binding region of the protein such that the antigen-binding region specifically binds human sperm protein 17 (Sp17).

2. The recombinant nucleic acid of claim 1, wherein:

the first variable domain comprises an amino acid sequence that is identical to SEQ ID NO: 3; and the second variable domain comprises an amino acid sequence that is identical to SEQ ID NO: 4.

3. The recombinant nucleic acid of claim 1, comprising a nucleotide sequence that is at least 70 percent identical to SEQ ID NO: 1.

4. The recombinant nucleic acid of claim 1, comprising a nucleotide sequence that encodes an amino acid sequence that is at least 90 percent identical to SEQ ID NO: 11.

5. The recombinant nucleic acid of claim 1, comprising a nucleotide sequence that is at least 70 percent identical to SEQ ID NO: 2.

6. The recombinant nucleic acid of claim 1, comprising a nucleotide sequence that encodes an amino acid sequence that is at least 90 percent identical to SEQ ID NO: 12.

7. The recombinant nucleic acid of claim 1, comprising an origin of replication, wherein the recombinant nucleic acid is a plasmid.

8. A cell, comprising the recombinant nucleic acid of claim 7, wherein the cell is a prokaryote.

9. A cell, comprising the recombinant nucleic acid of claim 1, wherein the cell is an immortalized mammalian cell.

10. The cell of claim 9, wherein the cell is a Chinese Hamster Ovary cell or a Human Embryonic Kidney cell; and wherein the cell expresses the protein.

11. The cell of claim 9, wherein the cell expresses a viral vector; and the recombinant nucleic acid comprises a packaging signal for packaging the recombinant nucleic acid in the viral vector.

12. A viral vector, comprising the recombinant nucleic acid of claim 1.

13. An isolated human cell, the cell comprising the recombinant nucleic acid as claimed in claim 1, wherein the human cell expresses the protein.

14. The isolated human cell of claim 13, wherein the human cell is a human peripheral blood mononuclear cell.

15. The isolated human cell of claim 13, wherein the human cell is a T-cell, a natural killer cell, or a monocyte.

16. The isolated human cell of claim 13, wherein the protein is a chimeric antigen receptor.

17. A Fab fragment of an antibody encoded by the recombinant nucleic acid of claim 1.

18. An antibody comprising the Fab fragment of claim 17.

19. A bi-specific antibody encoded by the recombinant nucleic acid of claim 1.

20. A bi-specific T-cell engager (BiTE) encoded by the recombinant nucleic acid of claim 1.

\* \* \* \* \*